(12) United States Patent
Robert et al.

(10) Patent No.: US 9,814,570 B2
(45) Date of Patent: Nov. 14, 2017

(54) OPHTHALMIC LENS COMBINATIONS

(71) Applicant: Abbott Medical Optics Inc., Santa Ana, CA (US)

(72) Inventors: Glick Robert, Lake Forest, CA (US); Brady Daniel, San Juan Capistrano, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 14/160,321

(22) Filed: Jan. 21, 2014

(65) Prior Publication Data
US 2014/0135921 A1      May 15, 2014

Related U.S. Application Data

(60) Division of application No. 11/456,521, filed on Jul. 10, 2006, now abandoned, which is a
(Continued)

(51) Int. Cl.
*A61F 2/16* (2006.01)
*G02C 7/00* (2006.01)
*A61F 2/00* (2006.01)

(52) U.S. Cl.
CPC .......... *A61F 2/1648* (2013.01); *A61F 2/1613* (2013.01); *A61F 2/1629* (2013.01); *G02C 7/00* (2013.01); *A61F 2002/009* (2013.01)

(58) Field of Classification Search
CPC ............................ A61F 2/1651; A61F 2/1602
(Continued)

(56) References Cited

U.S. PATENT DOCUMENTS

| 1,483,509 A | 2/1924 | Bugbee |
| 2,129,305 A | 9/1938 | Feinbloom |

(Continued)

FOREIGN PATENT DOCUMENTS

| AU | 3225789 A1 | 10/1989 |
| CH | 681687 A5 | 5/1993 |

(Continued)

OTHER PUBLICATIONS

Adler-Grinberg D., "Questioning Our Classical Understanding of Accommodation and Presbyopia," American Journal of Optometry & Physiological Optics, 1986, vol. 63 (7), pp. 571-580.
(Continued)

*Primary Examiner* — David H Willse
*Assistant Examiner* — Tiffany Shipmon
(74) *Attorney, Agent, or Firm* — Abbott Medical Optics Inc.

(57) ABSTRACT

An ophthalmic device is provided for a patient that has a basic prescription for distant vision, the ophthalmic device including a primary optic and a supplemental optic. The primary optic is configured for placement in the eye and has a base optical power configured to substantially provide the basic prescription. The supplemental optic has an optical power that is less than the optical power of the primary optic and is configured to provide, in combination with the primary optic, a combined optical power that provides the basic prescription of the patient. In addition, at least one surface of the primary optic is configured to deform in response to an ocular force so as to modify the combined optical power by at least 1 Diopter. The ophthalmic device may further include a movement assembly operably coupled to the primary optic that is structured to cooperate with the eye to effect accommodating deformation of the primary optic in response to an ocular force produced by the eye. The
(Continued)

movement assembly may also be configured to provide accommodating axial movement of the primary optic.

6 Claims, 5 Drawing Sheets

Related U.S. Application Data continuation-in-part of application No. 10/234,801, filed on Sep. 4, 2002, now abandoned, which is a continuation-in-part of application No. 09/390,380, filed on Sep. 3, 1999, now Pat. No. 6,616,692.

(60) Provisional application No. 60/132,085, filed on Apr. 30, 1999.

(58) Field of Classification Search
USPC .............................................. 623/6.32, 6.34
See application file for complete search history.

(56) References Cited

U.S. PATENT DOCUMENTS

| | | |
|---|---|---|
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,222,432 A | 12/1965 | Grandperret |
| 3,227,507 A | 1/1966 | Feinbloom |
| 3,305,294 A | 2/1967 | Alvarez |
| 3,339,997 A | 9/1967 | Wesley |
| 3,415,597 A | 12/1968 | Willard |
| 3,420,006 A | 1/1969 | Barnett |
| 3,431,327 A | 3/1969 | Tsuetaki |
| 3,482,906 A | 12/1969 | Volk |
| 3,507,565 A | 4/1970 | Alvarez et al. |
| 3,542,461 A | 11/1970 | Girard et al. |
| 3,583,790 A | 6/1971 | Baker |
| 3,617,116 A | 11/1971 | Jones |
| 3,632,696 A | 1/1972 | Jones |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |

(56) References Cited

U.S. PATENT DOCUMENTS

| | | |
|---|---|---|
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | De Carle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,834,749 A | 5/1989 | Orlosky |
| 4,840,627 A | 6/1989 | Blumenthal |
| 4,842,601 A | 6/1989 | Smith |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A * | 2/1991 | Richards ............... A61F 2/1629 623/6.32 |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Garabet |

(56) References Cited

U.S. PATENT DOCUMENTS

| | | |
|---|---|---|
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A * | 6/1998 | McDonald ............ A61F 2/1602 606/107 |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 * | 5/2001 | Lang ................ A61F 2/1613 623/6.24 |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skotton |
| 6,468,306 B1 | 10/2002 | Paul et al. |
| 6,474,814 B1 | 11/2002 | Griffin |
| 6,475,240 B1 * | 11/2002 | Paul ................ A61F 2/16 623/6.49 |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,685,315 B1 | 2/2004 | De Carle |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |

(56) References Cited

U.S. PATENT DOCUMENTS

| | | |
|---|---|---|
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 | 12/2004 | Willis et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 6,942,695 B1 | 9/2005 | Chapoy et al. |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,344,617 B2 | 3/2008 | Dubrow |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 2001/0001836 A1 | 5/2001 | Cumming |
| 2001/0004708 A1 | 6/2001 | Nagai |
| 2001/0012964 A1 | 8/2001 | Lang et al. |
| 2001/0016771 A1 | 8/2001 | Cumming |
| 2001/0018612 A1 | 8/2001 | Carson et al. |
| 2001/0039451 A1 | 11/2001 | Barnett |
| 2001/0044657 A1 | 11/2001 | Kellan |
| 2002/0002404 A1 | 1/2002 | Sarfarazi |
| 2002/0004682 A1 | 1/2002 | Zhou et al. |
| 2002/0011167 A1 | 1/2002 | Figov et al. |
| 2002/0045937 A1 | 4/2002 | Sarfarazi |
| 2002/0068971 A1 | 6/2002 | Cumming |
| 2002/0072795 A1 | 6/2002 | Green |
| 2002/0072796 A1 | 6/2002 | Hoffmann et al. |
| 2002/0095212 A1 | 7/2002 | Boehm |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0120329 A1 | 8/2002 | Lang et al. |
| 2002/0138140 A1 | 9/2002 | Hanna |
| 2002/0143395 A1 | 10/2002 | Skottun |
| 2002/0151973 A1 | 10/2002 | Arita et al. |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0018384 A1 | 1/2003 | Valyunin et al. |
| 2003/0020425 A1 | 1/2003 | Ricotti |
| 2003/0033013 A1 | 2/2003 | Callahan et al. |
| 2003/0050695 A1 | 3/2003 | Lin et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0074060 A1 | 4/2003 | Zadno-Azizi et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0093149 A1 | 5/2003 | Glazier |
| 2003/0105522 A1 | 6/2003 | Glazier |
| 2003/0109925 A1 | 6/2003 | Ghazizadeh et al. |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015235 A1 | 1/2004 | Worst et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0106992 A1 | 6/2004 | Lang et al. |
| 2004/0111151 A1 | 6/2004 | Paul et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0162612 A1 | 8/2004 | Portney et al. |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0049700 A1 | 3/2005 | Zadno-Azizi et al. |
| 2005/0055092 A1 | 3/2005 | Nguyen et al. |
| 2005/0060032 A1* | 3/2005 | Magnante ............... A61F 2/16 623/6.34 |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0113914 A1 | 5/2005 | Miller et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |

(56) References Cited

U.S. PATENT DOCUMENTS

| | | | |
|---|---|---|---|
| 2005/0137703 A1 | 6/2005 | Chen | |
| 2005/0228401 A1 | 10/2005 | Zadno-Azizi et al. | |
| 2005/0234547 A1 | 10/2005 | Nguyen et al. | |
| 2005/0246019 A1 | 11/2005 | Blake et al. | |
| 2005/0267575 A1 | 12/2005 | Nguyen et al. | |
| 2005/0288785 A1 | 12/2005 | Portney et al. | |
| 2006/0030938 A1 | 2/2006 | Altmann | |
| 2006/0064162 A1 | 3/2006 | Klima | |
| 2006/0095127 A1 | 5/2006 | Feingold et al. | |
| 2006/0098162 A1 | 5/2006 | Bandhauer et al. | |
| 2006/0100702 A1 | 5/2006 | Peyman | |
| 2006/0100703 A1 | 5/2006 | Evans et al. | |
| 2006/0111776 A1 | 5/2006 | Glick et al. | |
| 2006/0116764 A1 | 6/2006 | Simpson | |
| 2006/0116765 A1 | 6/2006 | Blake et al. | |
| 2006/0178741 A1 | 8/2006 | Zadno-Azizi et al. | |
| 2006/0184244 A1 | 8/2006 | Nguyen et al. | |
| 2006/0209430 A1 | 9/2006 | Spivey | |
| 2006/0209431 A1 | 9/2006 | Spivey | |
| 2006/0238702 A1 | 10/2006 | Glick et al. | |
| 2006/0259139 A1 | 11/2006 | Zadno-Azizi et al. | |
| 2006/0271187 A1 | 11/2006 | Zadno-Azizi et al. | |
| 2007/0027540 A1 | 2/2007 | Zadno-Azizi et al. | |
| 2007/0032866 A1 | 2/2007 | Portney | |
| 2007/0050025 A1 | 3/2007 | Nguyen et al. | |
| 2007/0067872 A1 | 3/2007 | Mittendorf et al. | |
| 2007/0078515 A1 | 4/2007 | Brady | |
| 2007/0088433 A1 | 4/2007 | Esch et al. | |
| 2007/0100444 A1 | 5/2007 | Brady et al. | |
| 2007/0100445 A1 | 5/2007 | Shadduck | |
| 2007/0106377 A1 | 5/2007 | Smith et al. | |
| 2007/0106379 A1 | 5/2007 | Messner | |
| 2007/0106381 A1 | 5/2007 | Blake | |
| 2007/0108643 A1 | 5/2007 | Zadno-Azizi et al. | |
| 2007/0123591 A1 | 5/2007 | Kuppuswamy et al. | |
| 2007/0129798 A1 | 6/2007 | Chawdhary | |
| 2007/0135915 A1 | 6/2007 | Klima | |
| 2007/0156236 A1 | 7/2007 | Stenger | |
| 2007/0213817 A1 | 9/2007 | Esch et al. | |
| 2007/0244561 A1 | 10/2007 | Ben Nun | |
| 2007/0258143 A1 | 11/2007 | Portney | |
| 2007/0260309 A1 | 11/2007 | Richardson | |
| 2007/0282247 A1 | 12/2007 | Desai et al. | |
| 2007/0299487 A1 | 12/2007 | Shadduck | |
| 2008/0004699 A1 | 1/2008 | Ben Nun | |
| 2008/0125790 A1 | 5/2008 | Tsai et al. | |
| 2008/0140192 A1 | 6/2008 | Humayun et al. | |
| 2008/0161913 A1 | 7/2008 | Brady et al. | |
| 2008/0161914 A1 | 7/2008 | Brady et al. | |
| 2008/0300680 A1 | 12/2008 | Joshua | |
| 2009/0012609 A1 | 1/2009 | Geraghty et al. | |
| 2009/0234448 A1 | 9/2009 | Weeber et al. | |
| 2009/0248152 A1 | 10/2009 | Bumbalough | |
| 2010/0057203 A1 | 3/2010 | Glick et al. | |
| 2010/0228346 A1 | 9/2010 | Esch | |
| 2011/0035001 A1 | 2/2011 | Woods | |
| 2012/0046744 A1 | 2/2012 | Woods et al. | |

FOREIGN PATENT DOCUMENTS

| | | | |
|---|---|---|---|
| DE | 2702117 A1 | 7/1978 | |
| DE | 3246306 A1 | 6/1984 | |
| DE | 4038088 A1 | 6/1992 | |
| DE | 19501444 * | 7/1996 | ............... A61F 2/16 |
| DE | 19501444 A1 | 7/1996 | |
| DE | 19951148 A1 | 4/2001 | |
| DE | 20109306 U1 | 8/2001 | |
| DE | 10059482 A1 | 6/2002 | |
| DE | 10125829 A1 | 11/2002 | |
| EP | 64812 A2 | 11/1982 | |
| EP | 162573 A2 | 11/1985 | |
| EP | 212616 A2 | 3/1987 | |
| EP | 246216 A2 | 11/1987 | |
| EP | 328117 A2 | 8/1989 | |
| EP | 329981 A1 | 8/1989 | |
| EP | 331457 A2 | 9/1989 | |
| EP | 336877 A1 | 10/1989 | |
| EP | 0337390 A2 | 10/1989 | |
| EP | 342895 A2 | 11/1989 | |
| EP | 351471 A2 | 1/1990 | |
| EP | 356050 A1 | 2/1990 | |
| EP | 337390 A3 | 5/1990 | |
| EP | 402825 A1 | 12/1990 | |
| EP | 420549 A2 | 4/1991 | |
| EP | 470811 A2 | 2/1992 | |
| EP | 478929 A1 | 4/1992 | |
| EP | 480748 A1 | 4/1992 | |
| EP | 488835 A1 | 6/1992 | |
| EP | 492126 A2 | 7/1992 | |
| EP | 507292 A1 | 10/1992 | |
| EP | 566170 A1 | 10/1993 | |
| EP | 601845 A1 | 6/1994 | |
| EP | 605841 A1 | 7/1994 | |
| EP | 691109 A1 | 1/1996 | |
| EP | 766540 A1 | 4/1997 | |
| EP | 779063 A1 | 6/1997 | |
| EP | 780718 A1 | 6/1997 | |
| EP | 897702 A2 | 2/1999 | |
| EP | 766540 B1 | 8/1999 | |
| EP | 1108402 A2 | 6/2001 | |
| EP | 1321112 A1 | 6/2003 | |
| EP | 1424049 A1 | 6/2004 | |
| EP | 1647241 A2 | 4/2006 | |
| EP | 1424049 B1 | 6/2009 | |
| FR | 488835 A | 11/1918 | |
| FR | 2666504 A1 | 3/1992 | |
| FR | 2666735 A1 | 3/1992 | |
| FR | 2681524 A1 | 3/1993 | |
| FR | 2745711 A1 | 9/1997 | |
| FR | 2778093 A1 | 11/1999 | |
| FR | 2784575 A1 | 4/2000 | |
| GB | 939016 A | 10/1963 | |
| GB | 2058391 A | 4/1981 | |
| GB | 2124500 A | 2/1984 | |
| GB | 2129155 A | 5/1984 | |
| GB | 2146791 A | 4/1985 | |
| GB | 2192291 A | 1/1988 | |
| GB | 2215076 A | 9/1989 | |
| JP | 0211134 | 1/1990 | |
| JP | H02126847 A | 5/1990 | |
| JP | H06508279 | 9/1994 | |
| JP | 7005399 A2 | 1/1995 | |
| JP | 7222760 A2 | 8/1995 | |
| JP | H09501856 A | 2/1997 | |
| JP | H09502542 A | 3/1997 | |
| JP | 10000211 A2 | 1/1998 | |
| JP | H11500030 A | 1/1999 | |
| JP | 11047168 A2 | 2/1999 | |
| JP | 2000508588 T2 | 7/2000 | |
| JP | 2003513704 T | 4/2003 | |
| JP | 2003190193 A | 7/2003 | |
| JP | 2003522592 T2 | 7/2003 | |
| JP | 2003525694 A | 9/2003 | |
| RU | 2014038 C1 | 6/1994 | |
| RU | 2014039 C1 | 6/1994 | |
| WO | WO-8404449 A1 | 11/1984 | |
| WO | WO-8603961 A1 | 7/1986 | |
| WO | WO-8700299 A1 | 1/1987 | |
| WO | WO-8707496 A1 | 12/1987 | |
| WO | WO-8803961 A1 | 6/1988 | |
| WO | WO-8902251 A1 | 3/1989 | |
| WO | WO-8911672 A1 | 11/1989 | |
| WO | WO-8911872 A1 | 12/1989 | |
| WO | WO-9000889 A1 | 2/1990 | |
| WO | WO-9109336 A1 | 6/1991 | |
| WO | WO-9302639 A1 | 2/1993 | |
| WO | WO-9305733 A1 | 4/1993 | |
| WO | WO-9416648 A1 | 8/1994 | |
| WO | WO-9503783 A1 | 2/1995 | |
| WO | WO-9610968 A1 | 4/1996 | |
| WO | WO-9615734 A2 | 5/1996 | |
| WO | WO-9625126 A1 | 8/1996 | |
| WO | WO-9635398 A1 | 11/1996 | |
| WO | WO-9712272 A1 | 4/1997 | |

(56) References Cited

FOREIGN PATENT DOCUMENTS

| | | |
|---|---|---|
| WO | WO-9727825 A1 | 8/1997 |
| WO | WO-9743984 A1 | 11/1997 |
| WO | WO-9805273 A1 | 2/1998 |
| WO | WO-9821621 A1 | 5/1998 |
| WO | WO-9849594 A1 | 11/1998 |
| WO | WO-9856315 A1 | 12/1998 |
| WO | WO-9903427 A1 | 1/1999 |
| WO | WO-9907309 A1 | 2/1999 |
| WO | WO-9920206 A1 | 4/1999 |
| WO | WO-9921491 A1 | 5/1999 |
| WO | WO-9929266 A1 | 6/1999 |
| WO | WO-0021467 A1 | 4/2000 |
| WO | WO-0027315 A1 | 5/2000 |
| WO | WO-0035379 A1 | 6/2000 |
| WO | WO-0046629 A1 | 8/2000 |
| WO | WO-0059407 A1 | 10/2000 |
| WO | WO-0061036 A1 | 10/2000 |
| WO | WO-0066037 A1 | 11/2000 |
| WO | WO-0066039 A1 | 11/2000 |
| WO | WO-0066040 A1 | 11/2000 |
| WO | WO-0066041 A1 | 11/2000 |
| WO | WO-0108605 A1 | 2/2001 |
| WO | WO-0119288 A1 | 3/2001 |
| WO | WO-0119289 A1 | 3/2001 |
| WO | WO-0128144 A1 | 4/2001 |
| WO | WO-0134061 A1 | 5/2001 |
| WO | WO-0134066 A1 | 5/2001 |
| WO | WO-0134067 A1 | 5/2001 |
| WO | WO-0156510 A1 | 8/2001 |
| WO | WO-0160286 A1 | 8/2001 |
| WO | WO-0164135 A1 | 9/2001 |
| WO | WO-0164136 A2 | 9/2001 |
| WO | WO-0166042 A1 | 9/2001 |
| WO | WO-0182839 A1 | 11/2001 |
| WO | WO-0189816 A1 | 11/2001 |
| WO | WO-0209620 A1 | 2/2002 |
| WO | WO-0212523 A2 | 2/2002 |
| WO | WO-0219949 A2 | 3/2002 |
| WO | WO-02058391 A2 | 7/2002 |
| WO | WO-02071983 A1 | 9/2002 |
| WO | WO-02098328 A1 | 12/2002 |
| WO | WO-03009051 A2 | 1/2003 |
| WO | WO-03015657 A2 | 2/2003 |
| WO | WO-03015669 A1 | 2/2003 |
| WO | WO-03034949 A2 | 5/2003 |
| WO | WO-03049646 A2 | 6/2003 |
| WO | WO-03057081 A2 | 7/2003 |
| WO | WO-03059196 A2 | 7/2003 |
| WO | WO-03059208 A2 | 7/2003 |
| WO | WO-03075810 A1 | 9/2003 |
| WO | WO-03084441 A1 | 10/2003 |
| WO | WO-03092552 A1 | 11/2003 |
| WO | WO-04000171 A1 | 12/2003 |
| WO | WO-2004020549 A1 | 3/2004 |
| WO | WO-2004037127 A2 | 5/2004 |
| WO | WO-2004073559 A1 | 9/2004 |
| WO | WO-2005011531 A2 | 2/2005 |
| WO | WO-2005018504 A1 | 3/2005 |
| WO | WO-2005019871 A2 | 3/2005 |
| WO | WO-03082147 A3 | 8/2005 |
| WO | WO-2005084587 A2 | 9/2005 |
| WO | WO-2005115278 A1 | 12/2005 |
| WO | WO-2006025726 A1 | 3/2006 |
| WO | WO-2006118452 A1 | 11/2006 |
| WO | WO-2007040964 A1 | 4/2007 |
| WO | WO-2007067872 A2 | 6/2007 |
| WO | WO-2008077795 A2 | 7/2008 |
| WO | WO-2008079671 A1 | 7/2008 |
| WO | WO-2008108524 A1 | 9/2008 |
| WO | WO-2009021327 A1 | 2/2009 |
| WO | WO-2010093823 A2 | 8/2010 |
| ZA | 8808414 A | 7/1989 |

OTHER PUBLICATIONS

Alcon Surgical, Alcon Laboratories.
Altan-Yaycioglu R., et al., "Pseudo-accommodation with Intraocular Lenses Implanted in the Bag," Journal of Refractive Surgery, 2002, vol. 18 (3), pp. 271-275.
Amo Specs Model AC-21 B, AMO Classic Series, 1992, 1 page.
CD New Elliptical Accommodating IOL for Cataract Surgery shown in Video type at ASCRS Symposium on Apr. 10, 1999.
Chauvin-Opsia, Azurite ACL (0459).
Chiron, Clemente Optfit Model SP525, Brochure Translation, Jul. 12, 1998.
Chrion Vision, Nuvita MA20, 1997, 1 page.
Cohen A.L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, 1992, vol. 31 (19), pp. 3750-3754.
Contact Lens Practice, 1998, pp. 211, 212, 403, 404, 491 and 792.
Co-pending U.S. Appl. No. 09/390,380, filed Sep. 3, 1999.
Co-pending U.S. Appl. No. 09/522,326, filed Mar. 9, 2000.
Co-pending U.S. Appl. No. 09/532,910, filed Mar. 22, 2000.
Co-pending U.S. Appl. No. 09/565,036, filed May 3, 2000.
Co-pending U.S. Appl. No. 09/631,223, filed Aug. 2, 2000.
Co-pending U.S. Appl. No. 09/656,661, filed Sep. 7, 2000.
Co-pending U.S. Appl. No. 09/657,251, filed Sep. 7, 2000.
Co-pending U.S. Appl. No. 09/657,325, filed Sep. 7, 2000.
Co-pending U.S. Appl. No. 09/721,072, filed Nov. 22, 2000.
Co-pending U.S. Appl. No. 09/795,929, filed Feb. 28, 2001.
Co-pending U.S. Appl. No. 09/822,040, filed Mar. 30, 2001.
Co-pending U.S. Appl. No. 10/020,853, filed Dec. 11, 2001.
Co-pending U.S. Appl. No. 10/280,918, filed Aug. 5, 2003.
Co-pending U.S. Appl. No. 10/280,937, filed Oct. 25, 2005.
Co-pending U.S. Appl. No. 10/635,423, filed Aug. 6, 2003.
Co-pending U.S. Appl. No. 11/618,325, filed Dec. 29, 2006.
Co-pending U.S. Appl. No. 11/618,411, filed Dec. 29, 2006.
Co-pending U.S. Appl. No. 11/966,365, filed Dec. 28, 2007.
DVD New Elliptical Accommodating IOL for Cataract Surgery shown at ASCRS Symposium on Apr. 1, 1999.
DVD titled "New Elliptical Accommodative IOL for cataract surgery" shown at ASCRS Symposium on Apr. 10, 1999.
English translation of Payer CH681687.
European Search Report for Application No. EP09009432, dated Aug. 27, 2009, 2 pages.
European Search Report for Application No. EP09178394, dated Jan. 25, 2010, 2 pages.
European Search Report for Application No. EP10181797, dated Jan. 28, 2011, 2 pages.
European Search Report for Application No. EP11152227, dated Oct. 21, 2011, 7 pages.
Extended European Search Report for Application No. EP11152508, dated Oct. 25, 2011, 7 pages.
Fechner P.U., et al., "Iris-Claw Lens in Phakic Eyes to Correct Hyperopia: Preliminary Study," Journal of Cataract and Refractive Surgery, 1998, vol. 24 (1), pp. 48-56.
Foldable Intraocular Lens Implants and Small Incision Cataract Surgery, Ohio Valley Eye Physicians, 2004.
Hanita Lenses, Source Ocular Surgery News International, 1 page.
Hara T., et al., "Accommodative Intraocular Lens with Spring Action Part 1 Design and Placement in an Excised Animal Eye," Ophthalmic Surgery, 1990, vol. 21 (2), pp. 128-133.
Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
International Preliminary Examination Report for Application No. PCT/US00/11565, dated Jun. 12, 2001, 11 pages.
International Preliminary Examination Report for Application No. PCT/US00/11731, dated Jul. 27, 2001, 11 pages.

(56) References Cited

OTHER PUBLICATIONS

International Preliminary Examination Report for Application No. PCT/US00/24715, dated Jan. 11, 2002, 5 pages.
International Preliminary Examination Report for Application No. PCT/US00/24832, dated Dec. 11, 2001, 6 pages.
International Preliminary Examination Report for Application No. PCT/US01/07062, dated Feb. 20, 2002, 2 pages.
International Preliminary Examination Report for Application No. PCT/US02/14850, dated Mar. 20, 2003, 2 pages.
International Preliminary Examination Report for Application No. PCT/US2001/023508, dated Oct. 31, 2002, 14 pages.
International Preliminary Examination Report for Application No. PCT/US2002/023908, dated Jun. 10, 2003, 3 pages.
International Preliminary Report on Patentability and Written Opinion for Application No. PCT/EP2007/063827, dated Oct. 12, 2010, 8 pages.
International Preliminary Report on Patentability and Written Opinion for Application No. PCT/US07/086832, dated Jun. 30, 2009, 9 pages.
International Preliminary Report on Patentability and Written Opinion for Application No. PCT/US07/086840, dated Aug. 11, 2009, 7 pages.
international Preliminary Report on Patentability and Written Opinion for Application No. PCT/US07/72275, dated Jan. 13, 2009, 10 pages.
International Preliminary Report on Patentability and Written Opinion for Application No. PCT/US09/038466, dated Sep. 28, 2010, 7 pages.
International Preliminary Report on Patentability and Written Opinion for Application No. PCT/US2004/29704, dated Mar. 13, 2006, 8 pages.
International Preliminary Report on Patentability and Written Opinion for Application No. PCT/US2004/41839, dated Jun. 20, 2006, 4 pages.
International Preliminary Report on Patentability and Written Opinion for Application No. PCT/US2006/036242, dated Apr. 1, 2008, 10 pages.
International Preliminary Report on Patentability and Written Opinion for Application No. PCT/US2006/41500, dated Apr. 29, 2008, 9 pages.
International Preliminary Report on Patentability and Written Opinion for Application No. PCT/US2006/61671, dated Jul. 1, 2008, 7 pages.
International Preliminary Report on Patentability and Written Opinion for Application No. PCT/US2007/089060, dated Aug. 30, 2011, 7 pages.
International Preliminary Report on Patentability and Written Opinion for Application No. PCT/US2010/039858, dated Jan. 4, 2012, 11 pages.
International Preliminary Report on Patentability and Written Opinion for Application No. PCT/US2010/039860, dated Jan. 4, 2012, 10 pages.
International Preliminary Report on Patentability and Written Opinion for Application No. PCT/US2010/044248, dated Feb. 7, 2012, 6 pages.
International Preliminary Report on Patentability and Written Opinion for Application No. PCT/US2010/047011, dated Feb. 28, 2012, 9 pages.
International Preliminary Report on Patentability for Application No. PCT/US2007/060112, dated Jul. 15, 2008, 1 page.
International Search Report and Written Opinion for Application No. PCT/US2010/023946, dated Feb. 22, 2011, 10 pages.
International Search Report for Application No. PCT/EP2007/063827, dated Oct. 5, 2010, 5 pages.
International Search Report for Application No. PCT/US00/11565, dated Sep. 8, 2000, 3 pages.
international Search Report for Application No. PCT/US00/11731, dated Aug. 21, 2000, 3 pages.
International Search Report for Application No. PCT/US00/24715, dated Feb. 27, 2001, 3 pages.
International Search Report for Application No. PCT/US00/24832, dated Dec. 12, 2000, 2 pages.
International Search Report for Application No. PCT/US01/07062, dated Aug. 24, 2001, 3 pages.
International Search Report for Application No. PCT/US01/23508, dated Jan. 15, 2002, 3 pages.
International Search Report for Application No. PCT/US02/14850, dated Aug. 12, 2002, 2 pages.
International Search Report for Application No. PCT/US07/086832, dated Sep. 11, 2008, 4 pages.
International Search Report for Application No. PCT/US07/086840, dated Jul. 27, 2009, 3 pages.
International Search Report for Application No. PCT/US07/72275, dated Sep. 9, 2008, 6 pages.
International Search Report for Application No. PCT/US09/038466, dated Sep. 17, 2009, 2 pages.
International Search Report for Application No. PCT/US2002/023908, dated Apr. 15, 2003, 1 page.
International Search Report for Application No. PCT/US2002/39428, dated Aug. 19, 2003, 5 pages.
International Search Report for Application No. PCT/US2003/01268, dated Nov. 3, 2003, 4 pages.
International Search Report for Application No. PCT/US2003/01270, dated Jun. 25, 2003, 5 pages.
International Search Report for Application No. PCT/US2003/34163, dated Apr. 12, 2004, 1 page.
International Search Report for Application No. PCT/US2003/34167, dated Sep. 2, 2004, 1 page.
International Search Report for Application No. PCT/US2004/29704, dated Jan. 25, 2005, 3 pages.
International Search Report for Application No. PCT/US2004/41839, dated May 11, 2005, 1 page.
International Search Report for Application No. PCT/US2006/36242, dated Feb. 7, 2007, 4 pages.
International Search Report for Application No. PCT/US2006/41500, dated Aug. 23, 2007, 5 pages.
International Search Report for Application No. PCT/US2006/61671, dated Apr. 5, 2007, 3 pages.
International Search Report for Application No. PCT/US2007/060112, dated Jun. 15, 2007, 2 pages.
International Search Report for Application No. PCT/US2007/089060, dated Apr. 24, 2008, 3 pages.
International Search Report for Application No. PCT/US2010/039858, dated Jan. 20, 2011, 3 pages.
International Search Report for Application No. PCT/US2010/039860, dated Dec. 14, 2010, 6 pages.
International Search Report for Application No. PCT/US2010/044248, dated Nov. 4, 2010, 4 pages.
International Search Report for Application No. PCT/US2010/047011, dated Feb. 16, 2011, 7 pages.
International Search Report for Application No. PCT/US99/26368, dated Apr. 11, 2000, 3 pages.
International Search Report for Application No. PCT/US99/29097, dated Apr. 14, 2000, 6 pages.
International Search Report for U.S. Application No. PCT/US2006/030606, dated Dec. 1, 2006, 3 pages.
IOL Technologie Brochure, MF4 The Autofocus Lens, 1995, 6 pages.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
JP2126847A—English Translation.
Klien S.A., "Understanding the Diffractive Bifocal Contact Lens," Optometry and Vision Science, 1993, vol. 70 (6), pp. 439-460.
Kuchle M., et al., "Implantation of a New Accommodative Posterior Chamber Intraocular Lens," Journal of Refractive Surgery, 2002, vol. 18 (3), pp. 208-216.
Lane S.S., et al., "Polysulfone Intracorneal Lenses," International Ophthalmology Clinics, 1991, vol. 31 (1), pp. 37-46.
Mandell R.B., "Contact Lens Practice", 4th Edition, Charles C. Thomas Publishers, 1988, 11 pages.

(56) References Cited

OTHER PUBLICATIONS

Mandell R.B., et al., "Mathematical Model of the Corneal Contour," 1965, School of Optometry, University of California, Berkeley, pp. 183-197.
Marron J.C., et al., "Higher-order Kinoforms," Computer and Optically Formed Holographic Optics, 1990, vol. 1211, pp. 62-66.
McCarey B.E., et al., "Modeling Glucose Distribution in the Cornea," Current Eye Research, 1990, vol. 9 (11), pp. 1025-1039.
Mediphacos Ltda, Ocular Surgery News International.
Menezo J.L., et al., "Endothelial Study of Iris-Claw Phakic Lens: Four Year Follow-Up," Journal of Cataract Refractive Surgery, 1998, vol. 24 (8), pp. 1039-1049.
Office Action dated Jul. 19, 2011 for Japanese Application No. 2006526344 filed Sep. 10, 2004.
Opthalmed Inc., OMAC-260.
Partial International Search Report for Application No. PCT/US2010/039858, dated Oct. 5, 2010, 2 pages.
Partial Program Re: ASCRS Symposium, Showing Video Tape Shown Between Apr. 10-14, 1999.
Pending Claims dated Jul. 29, 2009 for U.S. Appl. No. 11/618,411, filed Dec. 29, 2006.
Prosecution History for U.S. Appl. No. 10/958,871 (US20050234547) filed Oct. 5, 2004.
Prosecution History for U.S. Appl. No. 11/057,705 (US20060184244) filed Feb. 14, 2005.
Prosecution History for U.S. Appl. No. 11/195,422 (US20050267575) filed Aug. 1, 2005.
Prosecution History for U.S. Appl. No. 11/426,888, filed Jun. 27, 2006.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Randall Woods D.O., "The Woods Concept for Capsular Bag Placement," Copeland Intra Lenses, Inc.
Simonov A.N., et al., "Cubic Optical Elements for an Accommodative Intraocular Lens," Optics Express, 2006, vol. 14 (17), pp. 7757-7775.
Storz Opthalmics Inc., Model L122UV ACL.
Supplementary European Search Report for Application No. EP00980998, dated Sep. 11, 2007, 2 pages.
Supplementary European Search Report for Application No. EP02748257, dated Jun. 23, 2008, 2 pages.
Supplementary European Search Report for Application No. EP03777934, dated Jan. 26, 2010, 3 pages.
Supplementary European Search Report for Application No. EP03809651, dated Aug. 11, 2006, 2 pages.
Supplementary European Search Report for Application No. EP04814069, dated Jul. 12, 2007, 1 page.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
The Shah Bifocal Intraocular Lens Implant, Shah & Shah Intraocular Lens Laboratories, Calcutta, India, No Date.
Thornton S., "Accommodation in Pseudophakia," in: Percival SPB Color atlas of lens implantation, Chap. 25, St Louis, ed., Mosby, United States, 1991, pp. 159-162.
Universe IOL Center, Ocular Surgery News International.
Video presented by ASCRS Symposium of Cataracts IOL and Refractive Surgery at the ASOA Congress on Ophthalmic Practice Management. Clinical & Surgical Staff Program on Apr. 10-14, 1999 (VHS Tape).
Video Tape, "New Elliptical Acco. IOL for Cataract Surgery," shown at ASCRS Symposium on Apr. 10, 1999.
World Optics Inc., Ophthalmology Times, Mar. 15, 1995.
Written Opinion for Application No. PCT/US2007/060112, dated Jun. 15, 2007, 6 pages.

\* cited by examiner

OPHTHALMIC LENS COMBINATIONS

RELATED APPLICATION

This application is a Divisional of U.S. patent application Ser. No. 11/456,521, filed on Jul. 10, 2006, which is a Continuation-in-Part Application of U.S. patent application Ser. No. 10/234,801, filed Sep. 4, 2002, which is a Continuation-in-Part Application of U.S. patent application Ser. No. 09/390,380, filed Sep. 3, 1999, which claims the benefit of U.S. Provisional Application No. 60/132,085 filed Apr. 30, 1999. The disclosures of all the aforementioned are incorporated in their entirety by reference herein.

BACKGROUND OF THE INVENTION

Field of the Invention

The present invention relates generally to devices and methods for correcting vision and more particularly to ophthalmic device combinations for providing accommodative vision.

Description of the Related Art

The human eye includes an anterior chamber between the cornea and iris, a posterior chamber including a capsular bag containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near, intermediate and distant vision. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Multifocal IOLs without accommodating movement have also been used to provide near/far vision correction.

Attempts have been made to provide IOLs with accommodating movement along the optical axis of the eye as an alternative to shape changing. Examples of such attempts are set forth in Levy U.S. Pat. No. 4,409,691, U.S. Pat. Nos. 5,674,282 and 5,496,366 to Cumming, U.S. Pat. No. 6,176,878 to Gwon et al, U.S. Pat. No. 6,231,603 to Lang et al, and U.S. Pat. No. 6,406,494 to Laguette et al. The disclosure of each of these patents is incorporated herein by reference.

One problem that exists with such IOLs is that they often cannot move sufficiently to obtain the desired accommodation. The degree of accommodation has been closely related to the lens prescription of the individual patient. In addition, the presence of such lenses can result in cell growth from the capsular bag onto the optics of such lenses. Such cell growth, often referred to as posterior capsule opacification (PCO), can interfere with the clarity of the optic to the detriment of the lens wearer's vision.

Another problem that can occur is that of providing an intraocular lens that provides a predetermined amount of accommodative power for a wide variety of eyes and with a relatively low amount of aberrations for both near and distant vision. This problem may arise because mechanical stresses used to change the focal length of a lens generally give rise to optical aberrations that reduce visual acuity of the eye. A related problem is that of determining a precise prescription for the aphakic eye prior to the surgical procedure for replacing the natural lens with an accommodative intraocular lens. This may result in implantation of an intraocular lens that is either too strong or too weak for the patient, or that does not produce enough accommodation to provide both near and distant vision. A similar problem may occur when the correct prescription is initially provided, but the patient's prescription changes over time.

It would be advantageous to provide IOLs adapted for accommodating movement and/or deformation, which can preferably achieve an acceptable amount of accommodation and/or a reduced risk of PCO. It would also be advantageous to provide accommodating intraocular lenses or systems of ophthalmic devices that accurately provide a patient's prescription for distant and/or near vision in a way that produces little or no optical aberrations.

SUMMARY OF THE INVENTION

New combinations of ophthalmic devices such as intraocular lens combinations (ILCs) have been disclosed. Embodiments of the present invention provide distance, near and/or intermediate vision by axially moving and/or deforming one or more optical elements, for example, by deforming at least one optical surface (e.g., changing a radius of curvature or conic constant of the surface) and/or changing the thickness of the optic. The present combinations may be used to enhance the degree of accommodation achieved in spite of the movement and space limitations within the eye and to produce near and/or distant vision that is relatively low in optical aberrations. One advantage of the present combinations is the ability to standardize the prescription or optical power of the accommodating lens or optic of the combination. Thus, the required amount of movement and/or deformation in the eye to achieve accommodation can be substantially the same for all patients or for a particular class or category of patients. This greatly facilitates the design of the moving or deforming of the accommodating lens or optic. Further, with at least certain of the present combinations, improved inhibition of PCO is obtained. The present combinations may be designed to be relatively straightforward in construction, implanted or inserted into the eye using systems and procedures which are well known in the art, and be made to function effectively with little or no additional treatments or medications being required. In addition to changing the optical power of the eye, combinations of ophthalmic devices according to the present invention may also include a corrector lens or optic that is used in combination with an accommodating lens, wherein the corrector lens or optic is configured to correct monochromatic and/or a chromatic aberrations of a primary intraocular lens and/or of at least a portion of the ocular imaging system.

In one broad aspect of the present invention, intraocular lens combinations (ILCs) comprise a first optic body, second optic body and a movement assembly. The first optic body has a negative or plano optical power and is adapted to be placed in a substantially fixed position in a mammalian eye. In those cases where the first optic body has a negative optical power, it is also called the compensating optic body. The second optic body, also called the primary optic body, has a higher optical power than the first optic body. The movement assembly is coupled to the second optic body and is adapted to cooperate with the eye, for example, the zonules, ciliary muscle and capsular bag of the eye, to effect accommodating movement and/or accommodating deformation of the second optic body in the eye, for example, in response to one or more ocular forces or naturally occurring actions of the eye.

Advantageously, the second optic body has a high plus optical power to reduce the amount of movement, for example, axial movement, in the eye needed to provide accommodation for intermediate and near vision. The negative or minus optical power of the first optic body compensates for the excess plus or positive optical power in the first optic body. The use of such a compensating lens, that is the first optic body having a negative optical power, can allow for standardization of the optical power correction in the second optic body. In other words, the optical power of the second optic body, that is the primary or movable optic body, can be approximately equal from optic body to optic body, while the optical power of the first optic body, that is the compensating or fixed optic body, is adjusted from optic body to optic body to meet the specific vision correction needs (prescription) of each individual patient. Consequently, the required amount of movement of the second optic body in the eye can be approximately the same for all patients.

The present ILCs provide accommodation, preferably an acceptable degree of accommodation, in spite of movement and space limitations in the eye. For example, the maximum theoretical amount of axial movement for a simple disc lens having an overall diameter of 11 millimeters (mm) and an optic diameter of 5 mm that undergoes 1 mm of compression in its diameter is about 1.65 mm. The amount of axial movement required for a plus 15 diopter optic to provide 2.5 diopters of additional power in the spectacle plane is about 2.6 mm. However, a plus 30 diopter optic requires only 1.2 mm of axial movement to provide 2.5 diopters of additional power in the spectacle plane. Thus, by increasing the plus power of the second optic, which is adapted for accommodating movement, a reduced amount of movement is needed to achieve higher or enhanced degrees of accommodation. The first or fixed optic may have a minus power to compensate for the excess plus power in the second optic.

The present ILCs may include first and second optics with optical powers which provide a net plus optical power. To illustrate, assume that the patient requires a plus 15 diopter correction. The first optic body is provided with a minus 15 diopter optical power and the second optic body with a plus 30 diopter optical power. The net optical power of this ILC is approximately the sum of minus 15 diopters and plus 30 diopters or plus 15 diopters, the desired prescription for the patient in question. The powers of the first and second optics are only approximately additive since the net power of the combination also depends on other factors including, but not limited to, the separation of the two optics, the magnitude of the power of each individual optic body and its location in the eye and the like factors. Also, by adjusting the optical power of the first optic body, the net optical power of the ILC can be adjusted or controlled even though the optical power of the second optic body is standardized or remains the same, for example, at a plus 30 diopter optical power. By standardizing the optical power of the second optic body, the amount of movement in the eye required to obtain a given level of accommodation is substantially the same, and preferably well within the space limitations in the eye, from patient to patient.

In one very useful embodiment, the movement assembly comprises a member including a proximal end region coupled to the second optic body and a distal end region extending away from the second optic body and adapted to contact a capsular bag of the eye. Such movement assembly may completely circumscribe the second optic body or may be such as to only partially circumscribe the second optic body.

The second optic body preferably is adapted to be positioned in the capsular bag of the eye.

The first optic body may be coupled to a fixation member, or a plurality of fixation members, adapted to assist in fixating the first optic body in the eye. Each fixation member may have a distal end portion extending away from the first optic body. In one embodiment, the distal end portion of the fixation member is adapted to be located in the capsular bag of the eye. Alternately, the distal end portion of the fixation member may be located in contact with a sulcus of the eye. As a further alternate, the distal end portion of the fixation member may be adapted to be located in an anterior chamber of the eye.

The first optic body may be located posterior in the eye relative to the second optic body or anterior in the eye relative to the second optic body. In a useful embodiment, the first optic body is adapted to be positioned in contact with the posterior wall of the capsular bag of the eye. This positioning of the first optic body provides for effective compensation of the plus or positive vision correction power of the second optic body. In addition, by having the first optic body in contact with the posterior wall of the capsular bag, cell growth from the capsular bag onto the ILC, and in particular onto the first and second optics of the ILC, is reduced. This, in turn, reduces the risk of or inhibits posterior capsule opacification (PCO).

In one embodiment, the fixation member or members and the movement assembly are secured together, preferably permanently secured together. Thus, when inserting the ILC into the eye, a single combined structure can be inserted. This reduces the need to position the first and second optics relative to each other. Put another way, this feature allows the surgeon to very effectively and conveniently position the ILC in the eye with reduced surgical trauma to the patient.

The fixation member and movement assembly may be secured, for example, fused, together at the distal end portion of the fixation member and the distal end region of the movement assembly.

In an alternate embodiment, there is no connection between the fixation member or members of the compensating lens and the movement assembly of the primary lens. That is, the compensating lens and primary lens are completely separate from and independent of one another, enabling them to be implanted consecutively, rather than simultaneously. This allows the lenses to be inserted through a smaller incision than would be possible with a combined structure. In the case of separate lenses, however, special care must be taken to axially align the two lenses in order to avoid decentration issues.

In another broad aspect of the present invention, ILCs are provided which comprise a first optic body having a posterior surface adapted to be positioned in contact with a posterior wall of the capsular bag of the eye; a second optic body adapted to focus light toward a retina of the eye; and a movement assembly coupled to the second optic body and adapted to cooperate with the eye to effect accommodating movement of the second optic body in the eye. The first optic body has a substantially plano optical power or a negative optical power. These ILCs are particularly adapted to inhibit PCO.

The first optic body of these combinations preferably is adapted to be placed in a substantially fixed position in the eye. The posterior surface of the first optic body advantageously is configured to substantially conform to a major portion, that is, at least about 50%, of the posterior wall of the capsular bag of the eye in which the combination is placed. More preferably, the posterior surface of the first optic body is configured to substantially conform to substantially the entire posterior wall of the capsular bag. Such configuration of the first optic body is very useful in inhibiting cell growth from the eye onto the first and second optics and in inhibiting PCO.

In one embodiment, the first optic body, which contacts the posterior wall of the capsular, has a substantially plano optical power and the second optic body has a far vision correction power. In an alternate embodiment, the first optic body has a negative optical power and the second optic body has a positive optical power, so that the optical powers of the first and second optics provide a net plus optical power in the eye in which the combination is placed. In this latter embodiment, the second, or primary, optic body is preferably placed in the capsular bag, while the first, or compensating, optic body, may be placed in the bag, the sulcus or the anterior chamber, or attached to the iris.

In a very useful embodiment, the first optic body includes an anterior surface and at least one projection extending anteriorly from this anterior surface. The at least one projection is positioned to limit the posterior movement of the second optic body in the eye. Thus, the movement of the second optic body is effectively controlled to substantially maintain the configuration of the combination and/or to substantially maintain an advantageous spacing between the first and second optics.

The movement assembly may be structured and functions similarly to movement assembly of the previously described ILCS.

The first optic body may have a fixation member or members coupled thereto. The fixation member or members are adapted to assist in fixating the first optic body in the eye, that is in contact with the posterior wall of the capsular bag of the eye. In one embodiment, the first optic body itself is configured and/or structured so that no fixation member or members are needed to maintain the first optic body in contact with the posterior wall of the capsular bag of the eye. The first optic body and the movement assembly of these ILCs may be secured together.

In general, the first and second optics of the present ILCs may be made of any suitable materials. The first and second optics may be made of polymeric materials and, along with the movement assembly and any fixation member(s), are deformable for insertion through a small incision in the eye.

The present movement assemblies are sufficiently flexible to facilitate movement of the second optic body in the eye upon being acted upon by the eye. In one very useful embodiment, the movement assembly includes a hinge assembly that may be adapted and positioned to facilitate the accommodating movement of the second optic body.

In those embodiments in which the first optic body has a substantially plano optic body power, the second optic body preferably has a far vision correction power, more preferably such a power for infinity, in the unaccommodated state.

In a further broad aspect of the present invention, methods for inserting an ILC in an eye are provided. Such methods comprise providing an ILC in accordance with the present invention, as described herein. The ILC is placed into the eye, for example, in the capsular bag of the eye or partly in the capsular bag of the eye, using equipment and techniques which are conventional and well known in the art. The ILC is placed in a rest position in the eye, for example, a position so that the eye, and in particular the ciliary muscle and zonules of the eye, effectively cooperate with the movement assembly to move the second optic body of the ILC anteriorly in the eye from the rest position to provide for positive accommodation. No treatments or medications, for example, to paralyze the ciliary muscle, to facilitate fibrosis or otherwise influence the position of the ILC in the eye, are required.

In one embodiment, the primary and compensating lenses are connected by the fixation member or members and the movement assembly, and are thus simultaneously implanted in the eye. In another embodiment, the primary lens is implanted first and centered about the optical axis. The compensating lens is then inserted anteriorly of the primary lens and optically aligned with the primary lens. This latter embodiment may require a smaller incision than that required for the unitary combination of the former embodiment. In addition, this embodiment allows for refractive measurements to be made after the primary lens has been implanted, so that any new refractive errors that may have been introduced as a result of the surgery itself can be taken into account, and a more accurate prescription for the compensating lens can be obtained.

Preferably, the first and second optics and the movement assembly are deformed prior to being placed into the eye. Once the ILC is placed in the eye, and after a normal period of recovery from the surgical procedure, the ILC, in combination with the eye, provides the mammal or human wearing the ILC with effective accommodation, preferably with reduced risk of PCO. In the unaccommodated state, the ILC preferably provides the mammal or human wearing the ILC with far vision correction.

In certain embodiments, an accommodating ophthalmic device comprises a primary optic and supplemental optic. The primary optic is configured for placement in an eye of a subject or patient having a basic prescription (e.g., a basic prescription for distant vision or near vision) and has a base optical power that is selected to at least partially provide the basic prescription. In some embodiments, the base optical power is selected to be within 8 Diopters of the basic prescription, preferably within 4 Diopter of the basic prescription, and even more preferably within 2 Diopters of the basic prescription. The supplemental optic has an optical power that is selected to adjust or compensate for the base optical power and may be selected to have an optical power that is within a range of about −4 Diopters to +4 Diopters. The supplemental optic and the primary optic preferably have a combined optical power that is capable of providing the basic prescription of the patient to within 2 Diopters of the basic prescription, even more preferably within 1 Diopter of the basic prescription. In addition, at least one surface of the primary optic is configured to deform in response to an ocular force (e.g., contraction or relaxation of the ciliary muscle) so as to modify the combined optical power of the ophthalmic device or eye by at least 1 Diopter. The ophthalmic device may further comprise a movement assembly operably coupled to the primary optic that is structured to cooperate with the eye to effect accommodating deformation of the primary optic in response to an ocular force produced by the eye. The movement assembly may additionally or alternatively be configured to provide accommodating axial movement of the primary optic.

The primary optic of the accommodating ophthalmic device may be selected in accordance with the structure of the eye into which the primary optic is to be placed. In some embodiments, the supplemental optic is selected to change or adjust the optical power provided by the primary optic. In other embodiments, the supplemental optic is a corrector optic that is selected to correct the primary optic or a portion of the eye and that has either no optical power or an optical power that is within a range of about −4 Diopters to +4 Diopters. The corrector optic may be configured to correct a monochromatic aberration and/or a chromatic aberration of the primary optic and/or at least a portion of the eye (e.g., the cornea of the eye). For example, the corrector optic may be used to correct or compensate for an astigmatic aberration, a spherical aberration, and/or a comatic aberration.

The supplemental optic may be implanted together with the primary optic or separately from the primary optic (e.g., during a subsequent surgery from that in which the primary optic is implanted). The primary optic is preferably implanted within the capsular bag of the eye, but alternatively may be implanted outside the capsular bag, for example in the vicinity of the sulcus. The supplemental optic may also be implanted in the capsular bag in front of the primary optic; however, may alternatively be implanted anywhere in the anterior or posterior chambers of the eye. The primary and supplemental optic may be configured to maintain a separation between one another upon implantation within the eye or may be configured to contact one another in the eye. In some embodiments, the supplemental optic may be a corneal implant configured to be disposed within the cornea or a surface profile disposed on or within the cornea, the profile being formed by a laser (e.g., using a LASIK, LASEK, or PRK procedure).

In another aspect of the current invention, the supplemental optic is designed to provide a predetermined refractive outcome in terms of optical performance or image quality. In such embodiments, the supplemental optic may have an overall optical power that may be combined with the optical power of the primary optic to provide near vision, distant vision, or intermediate vision. Alternatively, the supplemental optic may have no or substantially no optical power. In either case, the supplemental optic is a corrector optic that is selected to correct an optical aberration, for example a spherical aberration of the eye and/or at least one surface of an optic of the ophthalmic device. In some embodiments, the supplemental optic is configured to favorably modify the aberrations when the primary optic is in an accommodative and/or disaccommodative state. In other embodiments, the supplemental optic is configured increase the depth of focus of the eye, for example, by changing the optical power or focal length of the supplemental optic as a function of distance from the optical axis thereof. In still other embodiments, the supplemental optic is configured to produce two or more simultaneous foci (e.g., a bifocal or multifocal lens).

In certain embodiment, the primary optic, the supplemental optic, and/or the corrector optic are part of a system or set of intraocular lenses for insertion into an eye. For example, the set of intraocular lenses may comprise a plurality of supplemental optics, each supplemental optic having a value of an optical characteristic that is different from the other supplemental optics of the plurality, at least one of the supplemental optics configured to provide, in combination with the primary optic, the basic prescription of the patient. The different optical characteristic may be a different optical power and/or a different amount of an optical aberration or some other optical characteristic (e.g., a different first order diffraction efficiency of a multifocal phase plate).

Any and all features described herein and combinations of such features are included within the scope of the present invention provided that the features of any such combination are not mutually inconsistent.

Further aspects and advantages of the present invention are set forth in the following detailed description and claims, particularly when considered in conjunction with the accompanying drawings in which like parts bear like reference numerals.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following figures, with like numerals indicating like parts.

DETAILED DESCRIPTION OF THE DRAWINGS

Figure 1:
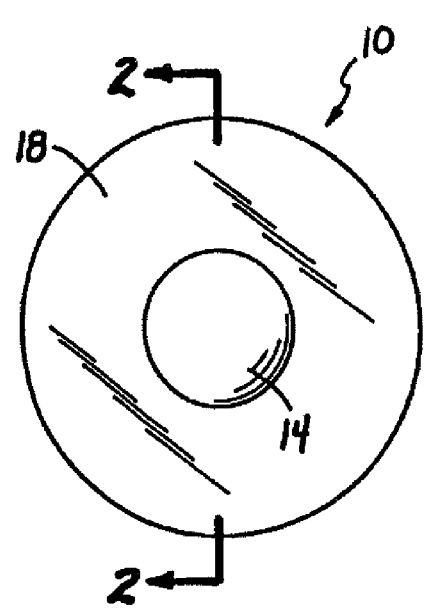
FIG. 1 is a front plan view of an ILC in accordance with the present invention.
Figure 2:
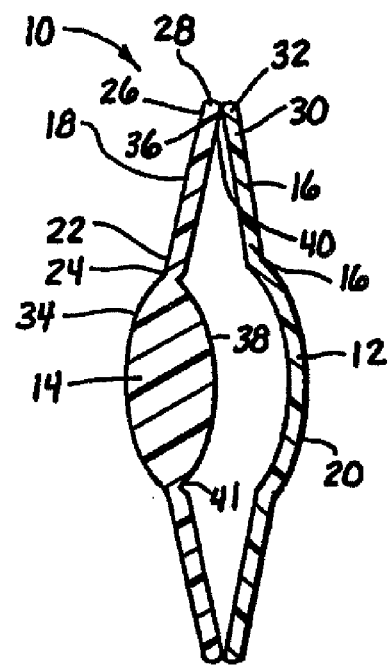
FIG. 2 is a cross-sectional view taken generally along line 2-2 of FIG. 1.

Referring now to FIGS. 1 and 2, an ILC according to the present invention, shown generally at 10, includes a first optic or optic body 12, a second optic or optic body 14, a disc type fixation member 16 and a disc type movement assembly 18. As used herein, the term "optic" or "optic body" means an optical element that may be used alone or as part of an optical system to produce an image on the retina the eye of a subject. The terms "optic" and "optic body" are used somewhat interchangeable, with the term "optic" emphasizing more the optical characteristics of an optical element and "optic body" referring more to the use an optical element as part of an intraocular lens that may also include, for example, a base element, a movement assembly, or one or more haptics, fixation members, and/or movement members. An optic or optic body may have an optic power to converge or diverge incident light using the principles of refraction, diffraction, and/or reflection of light. Alternatively, the optic or optic body may have substantially no optical power and/or be used to at least partially correct or compensate for an optical aberration, for example, by varying the optical characteristics of the optical element over the surface (e.g., as a function of radius from the center of the optical element). In addition, the optic or optic body may combine both optical power and aberration correction characteristics into a single optical element. Examples of aberration correction are found in U.S. Pat. Nos. 6,338,559 and 6,948,818, which are herein incorporated by reference.

The first optic body 12 has substantially plano optical power and is adapted to be held in a fixed position, for example, at least partially by the fixation member 16. When the ILC 10 is positioned in a human eye, the posterior surface 20 of first optic body 12 is in contact with the inner posterior wall of the capsular bag of the eye. This positioning of optic body 12 is very effective in reducing or inhibiting endothelial cell growth from the capsular bag onto the first optic body 12. In effect, the positioning of the first optic body 12 against the posterior surface of the capsular bag inhibits or reduce the risk of PCO.

The second optic body 14 includes a distance vision correction power. The movement assembly 18 extends radially outwardly from second optic body 14 and fully circumscribes the second optic body 14. Movement assembly 18 has a proximal end region 22 which is coupled to the second optic body 14 at first optic body periphery 24. Movement assembly 18 extends radially outwardly to a distal end region 26 including a peripheral zone 28.

Fixation member 16 includes a distal end portion 30 including a peripheral area 32. The movement assembly 18 and fixation member 16 are fused together at the peripheral zone 28 and peripheral area 32. Thus, the entire ILC 10 is a single unitary structure. The first optic body 12 and fixation member 16 can be manufactured separately from second optic body 14 and movement assembly 18 and, after such separate manufacture, the fixation member and movement assembly can be fused together. Alternately, the entire ILC 10 can be manufactured together. Also, if desired, the first optic body 12 and fixation member 16 can be inserted into the eye separately from the second optic body 14 and movement assembly 18. Thus, ILC 10 can comprise a plurality of separate components.

Movement assembly 18 extends outwardly from second optic body 14 sufficiently so that the distal end region 26, and in particular the peripheral zone 28 of the distal end region 28, is in contact with the inner peripheral wall of the posterior capsular bag when the ILC 10 is implanted in the eye.

As best seen in FIG. 2, when ILC 10 is at rest, the second optic body 14 is positioned vaulted anteriorly relative to the distal end region 26 of movement assembly 18. In other words, the anterior surface 34 of second optic body 14 is anterior of the anterior surface 36 of movement assembly 18 at distal end region 26 and/or the posterior surface 38 of the second optic body 14 is anterior of a posterior surface 39 of the movement assembly at the distal end region 26.

The first and second optics 12 and 14 may be constructed of rigid biocompatible materials, such as polymethyl methacrylate (PMMA), or flexible, deformable materials, such as silicone polymeric materials, acrylic polymeric materials, hydrogel polymeric materials, and the like, which enable the optics 12 and 14 to be rolled or folded for insertion through a small incision into the eye. Although the first and second optics 12 and 14 as shown are refractive lens bodies, the present ILCs can include at least one diffractive lens body, and such embodiment is included within the scope of the present invention.

As noted previously, first optic body 12 has a substantially plano or zero optical power. Second optic body 14 is prescribed for the wearer of ILC 10 with a baseline or far (distance) diopter power for infinity. Thus, the wearer of ILC 10 is provided with the vision correction power of second optic body 14 with little or no contribution from the first optic body 12.

The fixation member 16 and movement assembly 18, as shown, are integral (unitary) with and circumscribe the first and second optics 12 and 14, respectively. Alternately, fixation member 16 and/or movement assembly 18 can be mechanically or otherwise physically coupled to first optic body 12 and second optic body 14, respectively. Also, the fixation member 16 and/or movement assembly 18 may only partially circumscribe first and second optics 12 and 14, respectively, and such embodiments are included within the scope of the present invention. The fixation member 16 and movement assembly 18 may be constructed from the same or different biocompatible materials as first and second optics 12 and 14, and preferably are made of polymeric materials, such as polypropylene silicone polymeric materials, acrylic polymeric materials, and the like. Movement assembly 18 has sufficient strength and rigidity to be effective to transfer the force from the ciliary muscle of the eye so that the second optic body 14 is movable axially in the eye to effect accommodation.

Movement member 18 includes a region of reduced thickness 41 located at the proximal end region 22. This area of reduced thickness, which completely circumscribes the second optic body 14, acts as a hinge to provide additional flexibility to the movement member 18 to extenuate or amplify the accommodating movement of second optic body 14 in response to the action of the ciliary muscle and zonules.

The fixation member 16 and movement assembly 18 preferably are deformable, in much the same manner as first and second optics 12 and 14 are deformable, to facilitate passing ILC 10 through a small incision into the eye. The material or materials of construction from which fixation member 16 and movement assembly 18 are made are chosen to provide such members with the desired mechanical properties, e.g., strength and/or deformability, to meet the needs of the particular application involved.

The ILC 10 can be inserted into the capsular bag of a mammalian eye using conventional equipment and techniques, for example, after the natural crystalline lens of the eye is removed, such as by using a phacoemulsification technique. The ILC 10 may be rolled or folded prior to insertion into the eye, and is inserted through a small incision into the eye and is located in the capsular bag of the eye.

The ILC 10 in the eye is located in a position in the capsular bag so that the posterior surface 20 of first optic body 12 is maintained in contact with the inner posterior wall of the capsular bag. As noted previously, positioning the first optic body 12 in contact with the posterior wall of the capsular bag reduces the risk of or inhibits cell growth from the capsular bag onto the first optic body 12 which, in turn, reduces or inhibits PCO. The ciliary muscle and zonules of the eye provide force sufficient to move axially second optic body 14 sufficiently to provide accommodation to the wearer of ILC 10.

The ILC 10 should be sized to facilitate the movement of the second optic body 14 in response to the action of the ciliary muscle and zonules of the eye in which the ILC is placed.

If the ILC 10 is too large, the ciliary muscle and zonules will be inhibited from effectively contracting/relaxing so that the amount of accommodating movement will be unduly restricted. Of course, if the ILC 10 is too small, the second optic body 14 will be ineffective to focus light on the retina of the eye, may cause glare and/or the movement member may not cooperate with the eye to effect the desired amount of accommodating movement. If the ILC 10 is to be included in an adult human eye, the first and second optics 12 and 14 preferably have diameters in the range of about 3.5 mm to about 7 mm, more preferably in the range of about 5 mm to about 6 mm. The ILC 10 preferably has an overall maximum diameter, with the movement assembly 18 in the unflexed or rest state, in the range of about 8 mm to about 11 mm or about 12 mm.

The present ILC 10 has the ability, in cooperation with the eye, to move the second optic body 14 both posteriorly and anteriorly in the eye, to provide for both distance focus and near focus, respectively. This movement of ILC 10 advantageously occurs in response to action of the ciliary muscle and zonules, which action is substantially similar to that which effects accommodation in an eye having a natural crystalline lens. Thus, the ciliary muscle and zonules require little, if any, retraining to function in accordance with the present invention. The movement member 18, as described herein, preferably is effective to facilitate or even enhance or extenuate the axial movement of the second optic body 14 caused by the action of the ciliary muscle and zonules to provide increased degree of accommodation.

Figure 3:
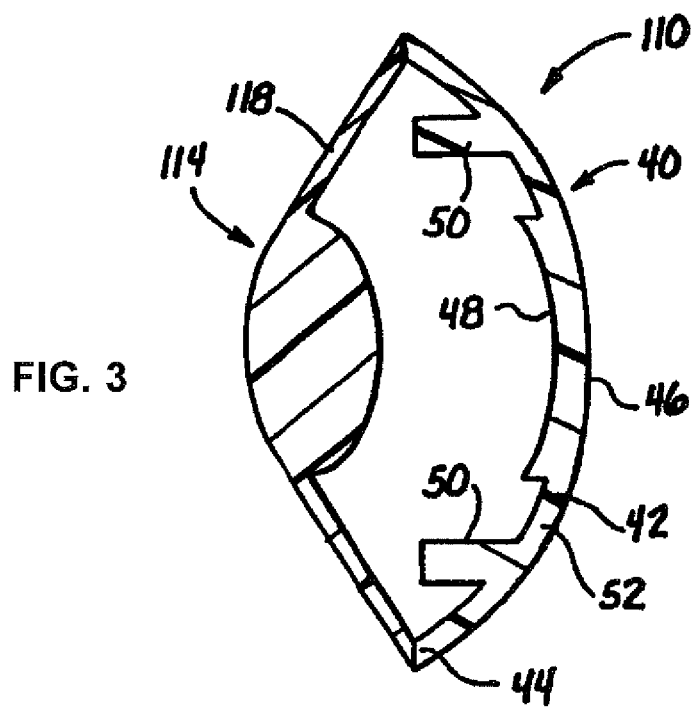
FIG. 3 is a cross-sectional view of an additional ILC in accordance with the present invention.

FIG. 3 illustrates an additional ILC, shown generally at 110, in accordance with the present invention. Except as expressly described herein, ILC 110 is structured and functions similar to ILC 10. Components of ILC 110 which correspond to components of ILC 10 are indicated by the same reference numeral increased by 100.

One primary difference between ILC 110 and ILC 10 relates to the substitution of a posterior lens structure 40 for the first optic body 12 and fixation member 16. Lens structure 40 includes a posterior face 42 which is configured to come in contact with and substantially conform to the inner posterior surface of the capsular bag of the eye in which the ILC 110 is to be placed. Thus, the surface 42 which extends around the peripheral area 44 and across the center region 46 of the lens structure 40 is adapted to come in contact with and substantially conform to the inner posterior wall of the capsular bag. Moreover, the lens structure 40 is adapted to remain in contact with this inner posterior wall of the capsular bag and to be fixed in the eye. This configuration has been found to be very effective in inhibiting cell growth from the eye onto the ILC 110. The anterior surface 48 of lens structure 40 is configured to provide the lens structure with a substantially plano or zero optical power. Second optic body 114 is prescribed for the wearer of ILC 110 with a baseline or distance or far (distance) dioptic power for infinity. Thus, the wearer of ILC 110 is provided with a vision correction power of second optic body 114 with little or no contribution from the lens structure 40.

Alternately, second optic body 114 has a high plus power, for example, plus 30 diopters. The lens structure 40, and in particular the region of the lens structure, defined by the anterior surface 48, which extends substantially across the entire field of vision of the wearer of ILC 110, has a minus vision correction power which is controlled to provide the correction prescription for use in the eye in which the ILC 110 is placed. For example, if this eye requires a plus 15 diopter power, the lens structure 40 has a vision correction power of approximately minus 15 diopters so that the net vision correction power of the combination of lens structure 40 and second optic body 114, is plus 15 diopters.

The lens structure can be made from materials described previously with regard to first optic body 12 and fixation member 16.

One additional feature of lens structure 40 relates to the anteriorly extending projections 50 which extend from the base element 52 of lens structure 40. The number of these projections 50 can range from 2 to about 6 or more. Alternately, a continuous annulus projecting anteriorly can be provided. The purpose of the projections 50 or the continuous annulus is to limit the posterior movement of the second optic body 114 and movement assembly 118. This limitation in the movement provides an additional degree of control of the ILC 110, and prevent a collapse of the ILC 110 and maintains an advantageous degree of separation between second optic body 114 and anterior surface 48 of lens structure 40.

Figure 4:
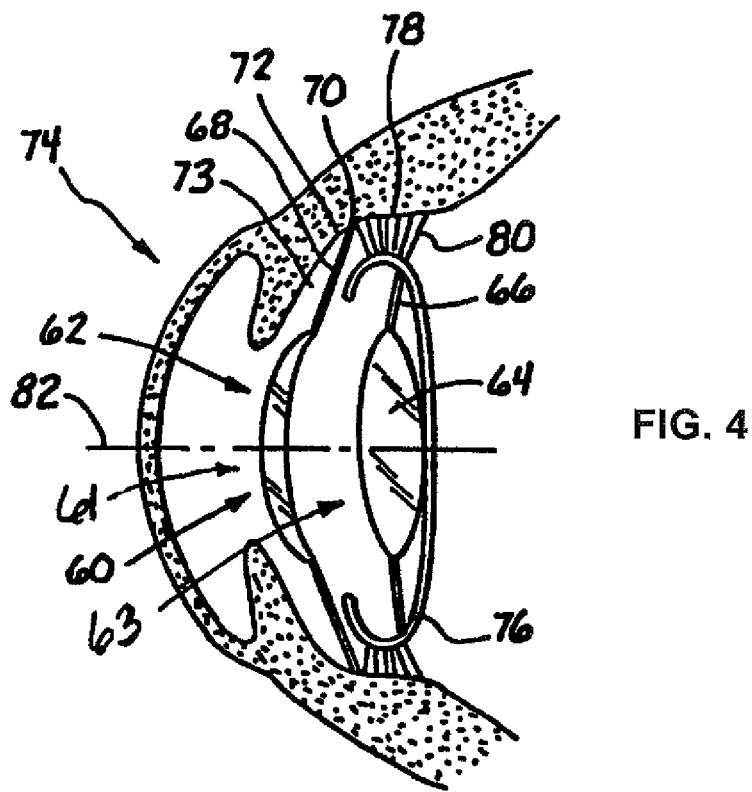
FIG. 4 is a fragmentary sectional view of an eye in which an alternate ILC in accordance with the present invention has been implanted.

FIG. 4 illustrates the use of an alternate ILC in accordance with the present invention. This ILC, shown generally at 60 includes a compensating IOL 61 comprising a first, or compensating, optic body 62, and a primary IOL 63 comprising a second, or primary, optic body 64 and a movement assembly 66. The compensating optic body 62 is coupled to a fixation member 68 which includes a distal end portion 70 in contact with the periphery 72 of the sulcus 73 of eye 74. Fixation member 68 is a disk fixation member which completely circumscribes the compensating optic body 62. However, it should be noted that the disc fixation member 68 can be replaced by two or more filament fixation members or plate fixation members or other types of fixation members, many of which are conventional and well known in the art. Movement assembly 66 is coupled to the primary optic body 64 and completely circumscribes the primary optic body. The primary optic body 64 is located in the capsular bag 76 of eye 74 and is vaulted anteriorly to some extent to enhance accommodating movement of the primary optic body.

The primary optic body 64 has a plus power higher than the power required by the basic prescription of a presbyopic patient. For instance for a patient requiring plus 15 diopters of far vision correction, primary optic body 64 might have a corrective power of plus 30 diopters. The compensating optic body 62 is a negative or minus lens having a minus vision correction power which is controlled to provide the correct prescription for use in eye 74. For the patient described above, the compensating optic body 62 has a vision correction power of approximately minus 15 diopters so that the net vision correction power of the combination of compensating optic body 62 and primary optic body 64 equals the patient's basic prescription of plus 15 diopters. The compensating optic body 62, fixation member 68, primary optic body 64 and movement assembly 66 can be made from materials described previously with regard to the first optic body 12, fixation member 16, second optic body 14 and movement assembly 18, respectively.

The compensating optic body 62 is shown here as a meniscus style optic body; that is, the anterior surface of the optic body is convex and the posterior surface is concave. However, other negative diopter configurations could also be used, such as plano/concave or biconcave. In addition, one or both of the surfaces of the compensating optic body 62 could be multifocal or aspheric to allow for additional accommodation.

In the configuration shown in FIG. 4, the fixation member 68 is in contact with the periphery 72 of the sulcus 73 of the eye 74. This is a relatively durable component of the eye and is effective to support the fixation member 68 in maintaining the compensating optic body 62 in a fixed position. The movement assembly 66 cooperates with the ciliary muscle 78 and zonules 80 of eye 74 to move the second optic body 64 axially along optical axis 82 of the eye. The amount of axial movement achieved will vary from patient to patient depending on such parameters as capsular bag dimensions. The movement is preferably at least about 0.5 mm, and more preferably at least about 0.75 mm. In a very useful embodiment, the accommodation assembly should allow about 1 mm to about 1.2 mm of movement. For example, with a primary optic body 64 having a corrective power of plus 30 diopters, this amount of movement will be amplified to create an additional add power, or diopter shift, of about 1.75 to about 2.5, or possibly as high as 3.5 diopters. A diopter shift in this range is consistent with the near vision, or add, prescription of a "typical" presbyopic patient. The movement assembly 66 may be configured to provide accommodative movement by producing relative motion between the optic body 64 and at least portion of the movement assembly 66. Alternatively, the movement assembly 66 may be configured to maintain a fixed or substantially fixed relationship between the optic body 64 and the movement assembly 66. In such embodiments, accommodation may be provided when both the movement assembly 66 and the optic body 64 move together relative to the retina of the eye as the capsular bag moves and/or changes shape during accommodation.

Figure 5:
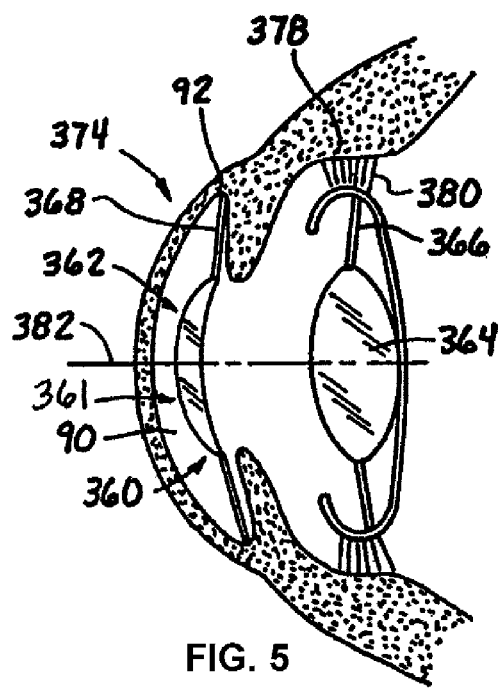
FIG. 5 is a fragmentary sectional view, similar to FIG. 4, in which the compensating optic body of the ILC is implanted in the anterior chamber of the eye.

FIG. 5 illustrates another ILC, shown generally at 360, in accordance with the present invention. Except as expressly described herein, ILC 360 is structured and functions similarly to ILC 60. Components of ILC 360 which correspond to components of ILC 60 are identified by the same reference numeral increased by 300.

One primary difference between TLC 360 and ILC 60 relates to the positioning of compensating optic body 362. Specifically, compensating IOL 361 is located in anterior chamber 90 of eye 374. Fixation member 368 is coupled to the compensating optic body 362 and extends outwardly and comes in contact with the angle 92 of eye 374. The arrangement of compensating optic body 362 and fixation member 368 is such that the compensating optic body is maintained in a substantially stationary position in the anterior chamber 90 of eye 374. The primary optic body 364 is adapted to be moved axially along optical axis 382 of eye 374 by the ciliary muscle 378 and zonules 380 acting on the movement assembly 366.

Figure 7:
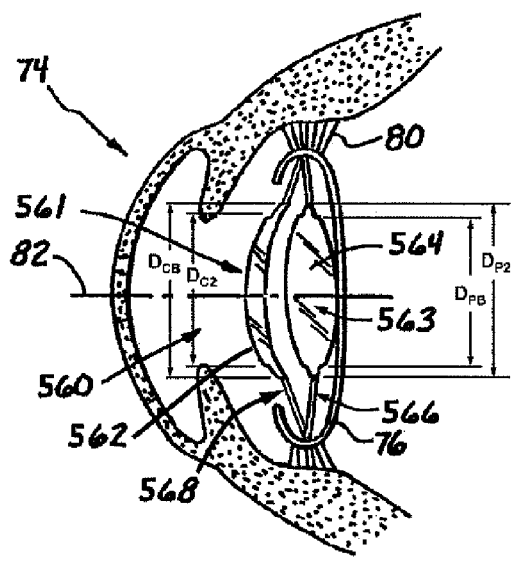
FIG. 7 is a fragmentary sectional view, similar to FIGS. 4 and 5, in which the compensating optic body of the ILC is implanted in the capsular bag of the eye.
Figure 8:
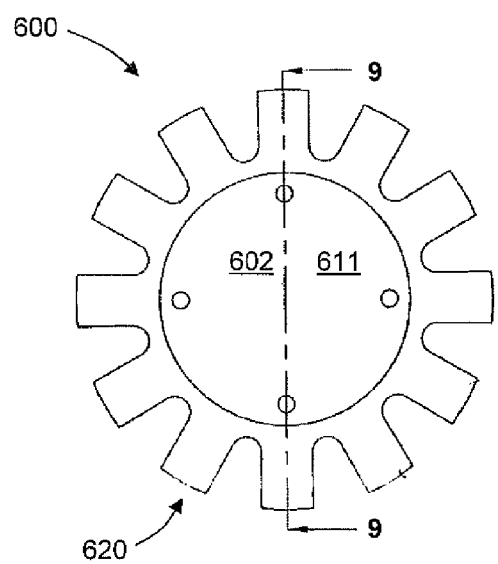
FIG. 8 is a front view of a primary lens according to another embodiment of invention having accommodative ability to provide both distant and near vision.
Figure 9:
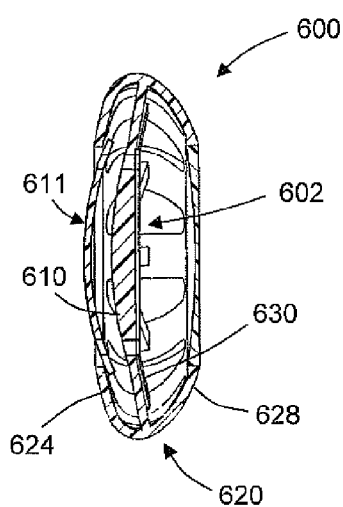
FIG. 9 is a cross-sectional view taken generally along line 9-9 of FIG. 8.

Still another embodiment of an ILC according to the present invention is shown in FIG. 7, indicated generally at 560. Except as expressly described herein, ILC 560 is structured and functions similarly to ILC 60. Components of ILC 560 which correspond to components of ILC 60 are identified by the same reference numeral increased by 500.

Again, ILC 560 differs from ILC 60 primarily in the location of the compensating IOL 561, which is located in the capsular bag 76 with the primary optic body 564, rather than in the sulcus or anterior chamber. In this configuration, the compensating optic body 562 would not be truly stationary since the capsular bag 76 itself typically moves about 0.4 mm during accommodation. However, axial movement of the compensating optic body 562 relative the capsular bag 76 can be limited by appropriate design of the fixation member or members 568. Controlling other factors such as material selection, length, width and angulation of the fixation member or members 58 relative the compensating optic body 562 can limit the overall axial movement of the compensating optic body 562 to less than 0.5 mm which, for the purposes of this invention, can be regarded as "substantially fixed."

A preferred method of implanting an ILC will now be discussed. The method is equally effective for the embodiments of FIGS. 5, 6, and 7, but for purposes of illustration will be discussed specifically with reference to FIG. 7.

Initially, the primary IOL 563 is inserted through an incision in the patients cornea and positioned in the capsular bag 76 using conventional techniques. Preferably, the incision is less than 4 mm in length. If the primary optic body 564 and movement assembly 566 are unitary as illustrated, they are inserted simultaneously. However, it is also possible to implant an independent movement assembly 566 first, and then insert the primary optic body in the movement assembly 566.

After the primary IOL 563 is placed in the capsular bag 76, a measurement is taken to determine the location of the primary optic body 564 relative to the optical axis 82. If desired, refractive measurements may also be made at this time to accurately determine an appropriate prescription for the compensating IOL 561.

If the original incision is still open, the compensating IOL 561 is inserted through the same incision using conventional techniques. If the incision has closed, a new one, preferably also measuring less than 4 mm, is made before insertion. A keratoscope or similar instrument is then used to guide the surgeon in positioning the fixation member or members 568 such that compensating optic body 562 and the primary optic body 564 are axially aligned with the optical axis 82 and one another. If necessary, the primary optic body 564 may also be repositioned at this time.

Alignment of the two optic bodies 562 and 564 is a crucial aspect of this invention, since any decentration of images will be amplified by the high diopter power of the primary optic body 564. Visual confirmation of alignment can be facilitated by providing the compensating optic body 562 with a diameter $D_{CB}$ equal to the diameter $D_{PB}$ of the primary optic body 564.

In addition, the ILC 560 can be made less sensitive to decentration by increasing the diameter of the optic zone, that is the portion of the optic body which has corrective power, in one or both of the IOLs 561 and 563. For instance, while the optic zones of prior art IOLs typically have a diameter in the range of about 3.5 mm to about 7 mm, the diameters of the optic zones $D_{PZ}$ and $D_{CZ}$ in IOLS 561 and 563, respectively, should be in the high end of that range or even higher, i.e. preferably from 5 mm to 8 mm. Even more preferably, at least one of the optic zone diameters $D_{PZ}$ or $D_{CZ}$ should be in the range of about 6.5 mm to about 8 mm. Although, as mentioned previously, the diameters $D_{PB}$ and $D_{CB}$ of the optic bodies 562 and 564 are preferably equal, the diameters $D_{PZ}$ and $D_{CZ}$ of the optic zones need not be.

Another factor influencing centration is the flexibility of fixation member or members 568. Preferably the member or members 568 are sufficiently flexible to allow the surgeon to reposition them as needed during the implantation process, but stiff enough to remain in a substantially fixed axial and radial position once implanted.

Figure 6:
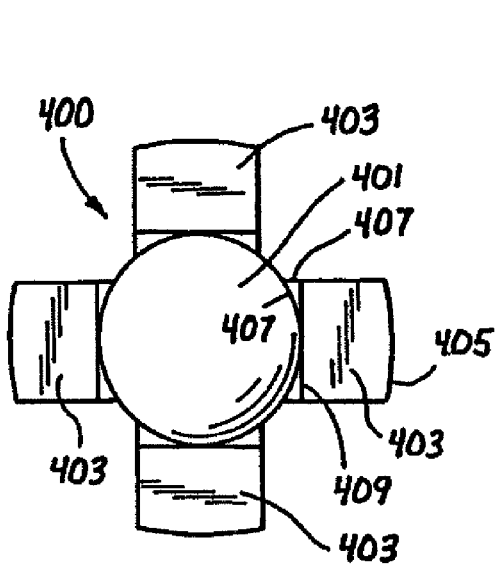
FIG. 6 is a front plan view of an intraocular lens useful in an ILC in accordance with the present invention.

FIG. 6 illustrates a still further embodiment of an intraocular lens in accordance with the present invention. This intraocular lens, shown generally at 400 includes an optic body 401 and four (4) equally spaced apart movement members 403. Each of the movement members 403 includes a distal region 405 and a proximal region 407 which is coupled to the optic body 401. A hinge, for example, a linear hinge, such as a reduced thickness area 409, is located near the proximal end 407 of each of the movement members 403. A linear hinge is particularly advantageous to achieve enhanced, or even substantially maximum theoretical, axial movement.

The IOL 400 can be used in place of the various second optic/movement assembly subcombinations noted above. One distinction between IOL 400 and these other subcombinations is the use of four (4) individual movement members 403 which do not totally circumscribe the optic body 401 relative to the movement assemblies noted previously which fully circumscribe the second optics. It should be noted that the movement assemblies of the present ILCs can have other configurations, for example, which are effective to facilitate or even enhance the movement of the second optics.

FIGS. 8-11 illustrate another embodiment of the present invention in which an ophthalmic device 600 comprises a primary optic 602 and a supplemental optic 604. The optics 602, 604 are configured for placement in an eye 607 of a patient or subject having a basic prescription (e.g., a basic prescription for distant or near vision) and are generally disposed about an optical axis 608. The primary optic 602 has a base optical power $P_{base}$ that may be selected to provide or approximately provide the basic prescription of the subject. For example, the base optical power may be selected to be within ±4 Diopters of the basic prescription, preferably within ±2 Diopters of the basic prescription, even more preferably within ±1 Diopter of the basic prescription.

The supplemental optic 604 comprises an anterior surface 605 and a posterior surface 606 that are configured to provide a supplemental optical power $P_{supplemental}$. In addition, the supplemental optic 604 may be configured to provide, in combination with the primary optic 602, a combined optical power $P_{combined}$ (e.g., $P_{base}+P_{supplemental}$) that is capable of providing the basic prescription of the patient. In certain embodiments, the supplemental optical power is selected or configured to modify the vision correction provided by the primary optic 602 by an amount that allows the combination to provide or substantially provide the basic prescription for at least one configuration of the primary optic 602. For example, the supplemental optical power may be selected such that the combined optical power is within 1 Diopter of the basic prescription. Generally, the primary optic 602 is configured to provide vision correction that is nearly equal to the patient's basic prescription for distant vision and the supplemental optic 604 is used to modify the vision correction provided by the primary optic 602 so as to more precisely provide the patient's basic prescription. In such cases, the supplemental optical power of the supplemental optic 604 is less than the primary optical power of the primary optic 602. For example, the primary optic 602 may have an optical power that is greater than 20 Diopters and the base optical power is greater than the supplemental optical power by at least 10 Diopters.

The ophthalmic device 600 is configured to produce ocular accommodation, for example, by configuring at least one surface of the primary optic 602 to be a deformable surface 610 that is able to deform in response to an ocular force. The resulting deformation may produce a change in the radius of curvature or of a conic constant of at least one surface of the primary optic 602. In addition, the thickness of the optic 602 is generally changed as it deforms. Deformation of the optic 602 generally results in a change in the optic properties of the optic 602, for example, a change in the optical power or aberrations produced by the optic 602.

The primary optic 602 is generally configured to produce an add power that modifies the primary optical power and/or the combined optical power by at least about 1 Diopter, preferably by at least 2 Diopters, and more preferably by at least 3 Diopters. The add power is a change in optical power that allows the eye to focus on objects that are at distances from about 30 cm to about 2 meters in addition to distant objects located at distances that are greater than 2 meters. The accommodative capability or add power provided by deformation of the surface 610 may be supplemented by axial motion or travel of the primary optic 602 along the optical axis 608 in response to the ocular force, as discussed in greater detail above.

As used herein, the term "ocular force" means any force produced by the eye of a subject that stresses, moves, or changes the shape of the natural lens of the eye or of at least a portion of an optic or intraocular lens that is placed in the eye of a subject. The ocular force acting on a lens (either a natural lens or an intraocular lens) may be produced, for example, by the state or configuration of the ciliary body (e.g., contracted or retracted), changes in the shape of the capsular bag of the eye, stretching or contraction of one or more zonules, vitreous pressure changes, and/or movement of some part of the eye such as the ciliary body, zonules, or capsular bag, either alone or in combination.

As used herein the terms "prescription" or "basic prescription" means an amount of optical power of a lens or an optic that is able to provide normal or functional vision to a subject when viewing objects located at a specified distances from the subject. For example, a "basic prescription for distant vision" is an amount of optical power for a lens or an optic that will allow a subject to resolve distant objects with a predetermined amount of visual acuity (e.g., to resolve the letters on a Snellen eye chart disposed at a distance of 20 feet from the subject with a visual acuity of at least 20/20, 20/30, or 20/40, based on the standard Snellen test for visual acuity).

As used herein the phrase "provide a basic prescription" (e.g., for distant, intermediate, or near vision) means to provide a lens or an optic that allows a subject to resolve objects at a specified distance with a predetermined degree of visual acuity (e.g., to resolve objects 20 feet from a subject with a visual acuity of at least about 20/40, more preferably of at least 20/30, and even more preferably of at least 20/20). As used herein, the phrase "substantially provide a basic prescription" (e.g., for distant vision or for near vision) means to provide an ophthalmic device, intraocular lens, or other internal optic that may be combined with an external lens, such as a spectacle lens or a contact lens, to allow a subject to resolve objects with a predetermined amount of visual acuity. The external lens typically has an optical power that is within a range of ±4 Diopters, preferably within a range of ±3 Diopters, and more preferably within a range of ±1 Diopter.

In certain embodiments, the primary optic 602 may be deformed by using a rigid optic 611 that is configured to deform the primary optic 602 in a predetermined manner, so as to produce accommodation or some other desired effect (e.g., changing the aberrations of the primary optic 602 and/or the wavefront that is directed to the retina of the eye 607). The optics 602, 611 are configured so that the deformable surface 610 is deformed when the optics 602, 611 are pressed together, as illustrated by comparing FIG. 10 with FIG. 11. Thus, the movement assembly 620 is structured to cooperate with the eye to effect accommodating axial movement of the primary optic 602 and accommodating deformation of the primary optic 602 in response to an ocular force produced by the eye 607.

The rigid optic 611 may be configured as a meniscus lens having no or substantially no optical power. Alternatively, the rigid optic 611 may be a meniscus or some other type of lens having either a positive or negative optical power and/or may have other optical properties such as the ability to compensate for optical aberrations and/or form a multifocal image on the retina when the eye 607 in an accommodative or disaccommodative state. In some embodiments, the rigid optic 611 has an optical power (and/or some other optical characteristic) and either replaces or supplements the supplemental optic 604. The structure and function of the movement assemblies similar to that movement assembly 620 in the illustrated embodiment are described in greater detail in U.S. Pat. No. 6,443,985, and U.S. Patent Application Publication Numbers 2004/082994 and 2004/0111153, which are all herein incorporated by reference.

One advantage of embodiments of the current invention is an increased ability to achieve a predetermined optical power or refractive outcome (e.g., the ability to resolve both distant objects and object at a reading distance of about 30 cm with a resolution of 20/30 or better). It will be appreciated that prior to implantation of an intraocular lens, the basic prescription for an aphakic eye and/or amount of accommodative capability of the eye may not be precisely known, since the precise contribution of the natural lens alone may not be precisely determinate. In certain embodiments of the present invention, the deformable primary optic 602 is implanted into the eye 607 to substantially provide the basic prescription for both distant and near vision (for example within ±2 Diopter). The patient may then be refracted in the usual manner to obtain a more accurately determination of the basic prescription for both distant and near vision. The optical power of the supplemental optic 604 may then be selected to provide the predetermined optical power or refractive outcome.

Another advantage of embodiments of the current invention is that a predetermined performance of an accommodating intraocular lens may be achieved when used in a variety of different eyes requiring intraocular lenses with different amounts of optical power. The inventors have observed that the image quality or amount of aberrations produced by a deformable optic change as the optic is deformed from one shape to another. The inventors have further observed that the amount of change in the image quality and/or aberrations can be controlled by proper selection of design parameters such as the thickness of the optic, the base optical power in an unstressed state, the material, etc. A primary optic 602 may be produced with a particular geometry and/or base optical power that has an optimized or predetermined optical performance over a range of add powers as compared to other geometries and/or base optical powers. This optimized primary optic 602 may be used in a variety of patients having different basic prescriptions to provide the same quality of accommodative performance for each. In order to provide each patient with their particular basic prescription, a different supplemental optic 604 with a different supplemental power for each, the supplemental optic 604 being selected in each case to provide the correct total power when used in combination with the primary optic 602.

Yet another advantage of embodiments of the current invention is that the supplemental optic 604 is a corrector optic that is selected to provide a predetermined refractive outcome in terms of optical performance or image quality of the eye and/or the ophthalmic device 600. In such embodiments, the supplemental optic 604 may have no or substantially no optical power or may have an optical power that is combined with the optical power of the primary optic 602 to provide near vision, distant vision, or intermediate vision. In some embodiments, the supplemental optic 604 enhances optical performance or image quality by correcting or reducing an aberration such as a chromatic aberration or a monochromatic aberration of the eye and/or ophthalmic device 600. For example, one or both of the surfaces 605, 606 of the supplemental 604 may be aspheric in form in order to reduce or compensate for a spherical aberration of the eye or ophthalmic device 600. Alternatively or additionally, at least one the surfaces 605, 606 be a monofocal or multifocal diffractive phase plate in order to reduce or compensate for a chormatic aberration of the eye or ophthalmic device 600. The supplemental optic 604 may be configured to favorably modify the aberrations when the primary optic 602 is in an accommodative and/or disaccommodative state.

In certain embodiments, the supplemental optic 604 is a corrector optic that is configured increase the depth of focus of the eye, for example, by changing the optical power or focal length of the supplemental optic 604 as a function of distance from the optical axis thereof. In other embodiments, the supplemental optic 604 is configured to produce two or more simultaneous foci (e.g., a bifocal or multifocal lens). In such embodiments, at least one of the surfaces 605, 606 of the supplemental optic 604 may comprise a diffractive phase plate that produces two or more diffraction orders. Alternatively, at least one of the surfaces 605, 606 may be configured to have an aspheric surface in which the radius of curvature varies with distance from the optical axis 608.

Figure 10:
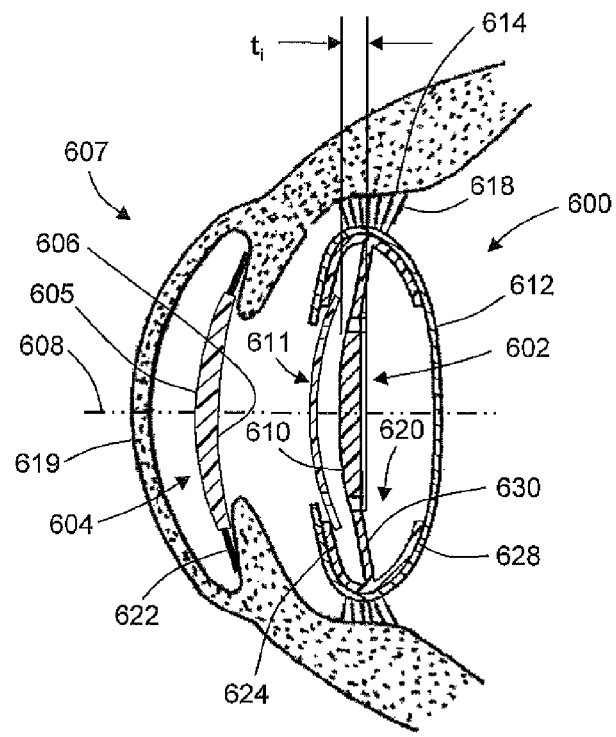
FIG. 10 is a cross-sectional view of an ophthalmic device according to an embodiment of the invention in an disaccommodative state, the device including the primary lens of FIG. 9 and a supplemental or corrector optic disposed within the anterior chamber of the eye.
Figure 11:
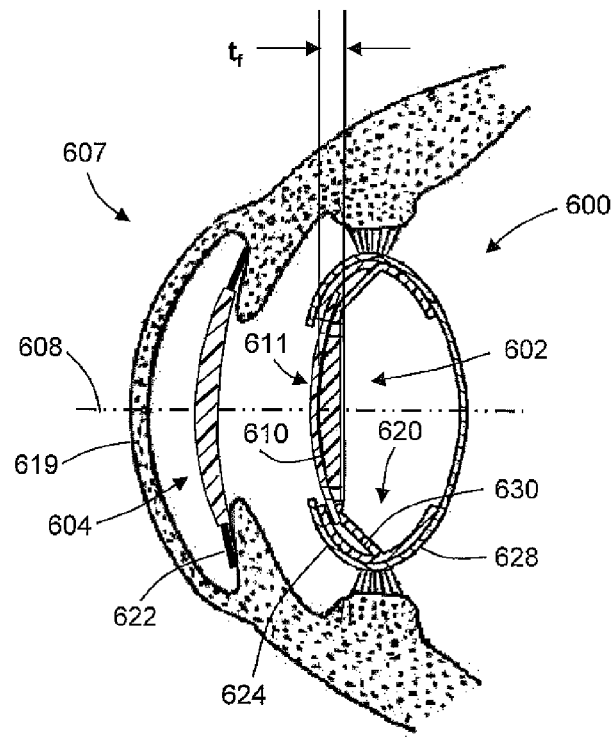
FIG. 11 is a cross-sectional view of the ophthalmic device shown in FIG. 10 in an accommodative state.

The primary optic 602 may be placed within a capsular bag 612, as illustrated in FIGS. 10 and 11, so that the ophthalmic device 600 is responsive to ocular forces produced by ciliary muscle 614 and/or zonules 618. Alternatively, the primary optic 602 may be implanted elsewhere within the eye 607. For example, the anterior and posterior capsules of the capsular bag 612 may be allowed to attach to one another and the ophthalmic device 600 implanted within the sulcus of the eye 607 so that the primary optic 602 is disposed in front of the capsular bag 612. In certain embodiments, the primary optic 602 has an optical power of at least about 10 Diopters, at least 20 Diopters, or at least 30 Diopters. In other embodiments, the primary optic 602 has a negative optical power, for example less than −5 Diopters, less than −10 Diopters, or less than −20 Diopters. In yet other embodiments, the primary optic 602 has an optical power within the range of −30 to +40 Diopters, −20 to +30 Diopters, or −10 to +20 Diopters.

In certain embodiments, a patient has a basic prescription for distant vision that is expressed in terms of an optical power $P_{distant}$. The difference between the optical power $P_{distant}$ and the base optical power $P_{base}$ of the primary optic 602 may be calculated and based on the ability of a surgeon or other practitioner to estimate the required basic prescription for distant vision, the primary optic 602 alone may be sufficient to restore both the distant and/or near vision of a patient to a degree that allows normal vision to be provided at least by the use of an external lens. In certain embodiments, the surgeon or practitioner is able to select the base optical power $P_{base}$ to be within ±4 Diopters of the basic prescription (e.g., abs $(P_{distant}-P_{base}) <= 4$ Diopters), preferably within ±2 Diopter of the basic prescription, more preferably within ±1 Diopter of the basic prescription. In other embodiments, the base optical power $P_{base}$ is within a range of zero to −4 Diopters of the basic prescription for distant vision, preferably within a range of zero to −2 Diopters, more preferably within a range of zero to −1 Diopters.

By selecting the optical power $P_{base}$ of the primary optic 602 to be within at least one of these ranges, the primary optic 602 is able to provide normal vision over at least some distances. For example, if ($P_{distant} - P_{base}$) is equal to −3 Diopters after implantation of the primary optic 602, the patient would have blurred distant vision, but a high degree of visual acuity at normal reading distances without the need for additional internal lenses (e.g. the supplemental optic 604) and/or external lenses (e.g., spectacles or contact lenses). In certain embodiments, the optical power $P_{supplemental}$ of the supplemental optic 604 is selected so that the combined optical power $P_{combined}$ is equal to or approximately equal to the basic prescription for distant vision (e.g., so that ($P_{distant} - P_{combined}$) is approximately equal to zero).

The supplemental optic 604 may be configured to be implanted together with the primary optic 602 or separately therefrom. In some embodiments, the supplemental optic 604 is only optionally implanted into the eye 607 when the actual vision provided by the primary optic 602 differs by a predetermined amount from an expected refractive outcome and/or the prescription of the patient changes by predetermined amount over time after initial implantation of the primary optic 602 and/or supplemental optic 604. The supplemental optic 604 may be disposed in front of the iris or in the anterior chamber of the eye 607, as illustrated for example in FIGS. 10 and 11. Alternatively, the supplemental optic 604 may be disposed within the vicinity of the sulcus of the eye 607, together with the primary optic 602 within capsular bag 612, or slightly protruding from the capsular bag 612. In other embodiments, the supplemental optic 604 may be disposed within a cornea 619 of the eye as a corneal implant. In yet other embodiments, the supplemental optic 604 may be a corneal implant disposed configured to be disposed within the cornea 619 or a surface profile disposed on or within the cornea 619, the profile being formed by a laser (e.g., using a LASIK, LASEK, or PRK procedure).

The primary and supplemental optics 602, 604 may be configured and disposed within the eye 607 so as to maintain a separation therebetween that is greater than a predetermined minimum, for example 200 micrometer, 500 micrometers, or about 1 millimeter. Alternatively, the primary and supplemental optics 602, 604 may be configured and disposed within the eye 607 so as to press against one another while the eye 607 is in an accommodative and/or disaccommodative state and/or between an accommodative and a disaccommodative state.

At least one surface of the primary optic 602, for example the deformable surface 610, is configured to deform in response to an ocular force so as to modify the optical power of at least one of (1) the primary optic 602, (2) the combined optical power of the optics 602, 604, and/or (3) the total or effective optical power of the entire eye 607. The deformation may be the result of change in the radius of curvature as the primary optic 602 changes from an accommodative state and disaccommodative state, which results in a change in the optical power or focal length of the primary optic 602. Alternatively or additionally, at least one surface of the primary optic 602 may change from a spherical profile to an aspheric profile or from a more spherical profile to a less spherical profile as the primary optic 602 changes from an accommodative state and disaccommodative state, or visa versa, wherein the profile change produces a change in optical power or in some other optical characteristic of the primary optic 602. In other embodiments, the primary optic 602 may change from a monofocal lens to a multifocal lens (either refractive or diffractive) as the primary optic 602 changes from an accommodative state and disaccommodative state, or visa versa. Alternatively, the primary optic 602 may be a multifocal lens, wherein the optical power or some other optical characteristic of the zones changes as the primary optic 602 changes between accommodative state and disaccommodative states.

In certain embodiments, the primary optic 602 has a center thickness $t_i$ along the optical axis 608 when in a substantially unstressed state and a center thickness $t_f$ in the response to or in the absence of an ocular force. In such embodiments, the primary optic 602 may be adapted to change the center thickness by a factor of at least 1.1 (e.g., the quotient $t_f/t_i$ is at least 1.1), typically when the ocular force is in the range of about 1 to 10 grams, preferably in the range of about 5 to 10 grams. In other embodiments, the primary optic 602 is adapted to change the center thickness by a factor of at least 1.05 or at least 1.2 or more. In yet other embodiments, the primary optic 602 is adapted to change the center thickness by a factor of at least 1.05, 1.1, or 1.2 when the ocular force is in the range of about 1 to 5 gram or about 1 to 3 grams. In still other embodiments, the primary optic 602 has a center thickness along the optical axis 608 when the primary optic 602 is in a substantially unstressed state, the deformable optic adapted to change the center thickness by at least about 50 micrometers, preferably at least 100 micrometers, when the ocular force is in the range of about 1 to 9 grams, in the range of about 6 to 9 grams, or in the range of about 1 to 3 grams. Within the art, an understanding of the physiology of the eye is still developing. Thus, other ranges of ocular forces able to provide the above ranges of relative and/or absolute thickness change are anticipated as the physiology of the eye is better understood. Such ranges of ocular forces are also consistent with embodiments of the present invention as disclosed herein.

The modification in optical power as the primary optic 602 deforms is preferably at least 1 Diopter, more preferably at least 2 Diopters or 3 Diopters, and even more preferably at least 2 to 4 Diopters or 3 to 5 Diopters. The amount of change in optical power of primary optic 602 is generally an effective Diopter change in the optical power, for example, from a principal plane of the primary optic 602 (e.g., somewhere between the anterior and posterior surfaces of primary optic 602). In general, and as illustrated in FIGS. 10 and 11, the Diopter change may be a positive change as the ciliary muscle 614 contracts and the zonules 618 relax; however, other directions and/or types of Diopter change are allowable (e.g., multifocal and/or aberration changes).

In the illustrated embodiment, the ophthalmic device 600 comprises a movement assembly 620 that is operably coupled to the primary optic 602 and a fixation member 622 that is operably coupled to the supplemental optic 604. Alternatively, the supplemental optic 604 may be coupled to the movement assembly 620 or comprise its own, separate movement assembly. The movement assembly 620 comprises an anterior portion 624 that engages the anterior capsule of the capsular bag 612 and a posterior portion 628 that engages the posterior capsule of the capsular bag 612. The anterior and posterior portions 624, 628 together form an enclosure that fills or substantially fills the capsular bag 612. The movement assembly 620 may further comprise a plurality of arms 630 that are configured to pivot, rotate, bend and/or otherwise deform in response to deformation of the movement assembly 620, whereby the primary optic 602 may be moved and/or deformed to provide accommodation.

The anterior and posterior portions 624, 628 are generally made of a resilient material (e.g., a silicone or acrylic material) that deforms in response to an ocular force in such a way that the movement assembly 620 conforms and remains in contact with the capsular bag 612 during accommodative movement thereof.

The embodiment illustrated in FIGS. 8-11 of the primary optic 602, the supplemental optic 604, and structures connected to the optics 602, 604 is exemplary only and is not meant to limit the scope of the invention. For example, the primary optic 602 may be configured to have a posterior vault rather than the anterior vault illustrated in FIGS. 10 and 11, in which case the deformable surface 610 is pressed against the posterior capsule of the capsular bag 612 when the ciliary muscle 614 contracts and the shape of the capsular bag 612 changes. In certain embodiments, the ILC illustrated in FIG. 7 is used to provide such a configuration, wherein the posteriorly vaulted primary IOL 563 is made of a material that is sufficiently soft to deform in response to ocular forces and the compensating IOL 561 is configured as a supplemental optic. Other examples of devices and means for producing a predetermined amount of accommodation in response to an ocular force may be found, for example, in U.S. patent application Ser. No. 11/241,586, which is herein incorporated by reference.

Figure 12:
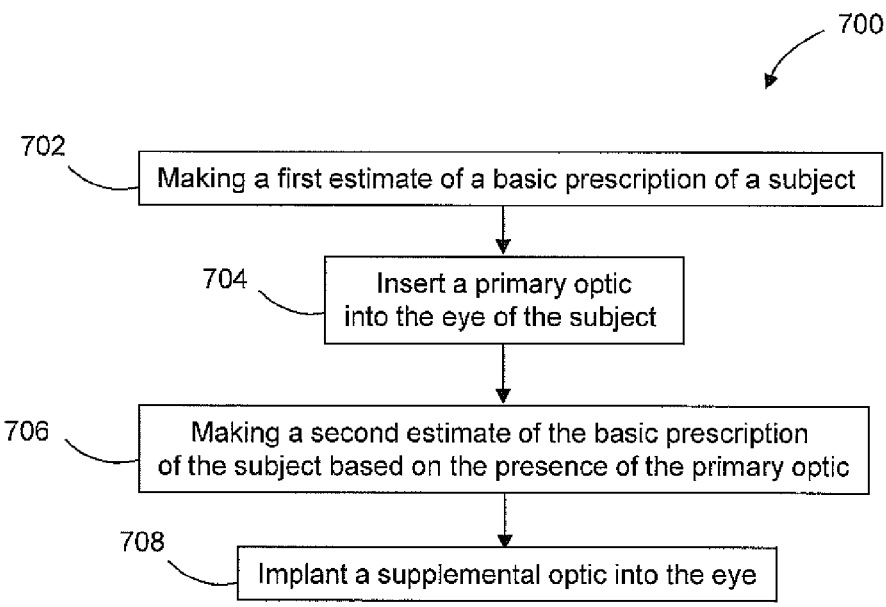
FIG. 12 is block diagram of a method of providing accommodative vision according to an embodiment of the invention.

The ophthalmic device 600 may be used in a surgical procedure to restore both distant vision and accommodative ability for providing near vision. Referring to FIG. 12, in some embodiments, a method 700 of providing accommodative vision comprises an operational block 702, making a first estimate of a basic prescription of a subject. The method 700 also comprises an operational block 704, inserting the primary optic 602 into the eye 607 of the subject. The method 700 further comprises an operational block 706, which includes making a second estimate of the basic prescription of the subject based on the presence of the primary optic 602. The method additionally comprises an operational block 708, implanting the supplemental optic 604 into the eye 607.

In the operational block 702, the surgeon make a first estimate of the basic prescription of the patient by, for example, measuring physical characteristic of the eye such as the axial length (AL) and the anterior chamber depth (ACD). Other dimensional parameters may also be measured including, but are not limited to, the corneal radius (CR), the corneal power (K), and crystalline lens thickness (LT). The first estimate may also include other parameters of the eye such as the refractive indices and/or estimated refractive indices of the various portions of the eye. The estimate may additionally or alternatively include performing one or more interactive vision tests with the subject, for example using the standard Snellen test for visual acuity. Generally, the first estimate is determined while the natural lens or a previously implanted intraocular lens is still in the eye. In some embodiments, the first estimate may be made after removal of the natural lens and/or explanting a previously implanted intraocular lens.

In some embodiments, the estimates of the basic prescription are made using ophthalmic instruments designed to measure physical properties of the eye or wavefront aberrations produced by the eye, for example using biometry or keratometry. Corneal surface measurements according to well-known topographical measurement methods may be used that express surface irregularities of the cornea. Corneal measurements for this purpose can be performed by the ORBSCAN® videokeratograph available from Orbtech or by corneal topography methods, such as EyeSys® available from Premier Laser Systems. The corneal measurements may also include the measurement of the corneal refractive power. In addition, wavefront sensors such as the Hartmann-Shack sensor (J. Opt. Soc. Am., 1994, Vol. 11(7), pp. 1949-57) may also be used to determine aberrations of the eye. The wavefront sensor may be used in combination with topographic sensors to determine other physical characteristics of the eye such as its length.

In the operational block 704, the surgeon implants the primary optic 602 into the eye 607. In certain embodiments, the primary optic 602 is selected to have a base optical power $P_{base}$ that substantially provides the basic prescription and is within at least ±4 Diopters of the basic prescription. Since the primary optic 602 substantially provides a basic prescription and in addition has the ability to provide accommodation, the primary optic 602 advantageously allows a surgeon to use a single implanted optic to provide a patient both distant and near vision. In some cases, satisfactory distant vision and near vision may be restored using only the primary optic 602, without the need of implanting the supplemental optic 604 or using other external lenses. In other cases, the basic prescription is provided only for certain distances or the vision provided is within an acceptable range to allow a more accurate estimate of a patient's prescription for both near and distant vision. In such cases, both distant and near vision may be restored using a single prescription spectacle or contact lens, since the primary optic 602 provides accommodative ability. Alternatively, the supplemental optic 604 may be implanted to restore full vision of both distant and near objects. In addition, because the primary optic 602 is able to substantially provides the basic prescription, a more accurate estimate of the aberrations of eye 607 may be made and subsequently corrected or compensated for using either an external optic and/or the supplemental optic 604.

In operational block 706, the surgeon may make the second estimate of the basic prescription either at the time of the surgery or at a time shortly after the implantation of the primary ophthalmic device 600. Alternatively, the second estimate may be made at a later time by the surgeon or by another practitioner, such as an optometrist, after the subject has more fully recovered from the surgical procedure. In some instances, the time between the implantation of the primary optic 602 and the second estimate is an extended period of time in order to allow the eye to recover from the surgical procedure. The period of time may be one week, one month, or even several months (from at least about three months to at least about 6 months). Also, in some cases, the basic prescription may change some time after implantation of the primary optic 602 (perhaps for causes unrelated to the surgical procedure), thereby necessitating a second estimate and correction of the subject's vision. In cases where an implanted supplemental optic 604 must be explanted in order to restore proper vision, the difficulty of explanting is advantageously reduced using the ophthalmic device 600, since the supplemental optic 604 may be made relatively thin and is disposed in front of the primary optic 602 and nearer to the front of the eye 607 (e.g., in the anterior chamber in the illustrated embodiment).

In certain embodiments, the primary optic 602 and/or the supplemental optic 604 belong to a system or set of intraocular lenses. In some embodiments, the set of optics comprises a single primary optic 602 and a set or plurality S1 of supplemental optics 604. The single primary optic 602 may be configured to provide an approximate correction for predetermined population, for example a population of patients with eyes having a particular range of axial lengths or type or shape of cornea, while the supplemental optic 604 is selected from the set S1 of supplemental optics 604 to provide a more precise correction for a particular individual within the population. The primary optic 602 may have a base optical power selected to be at or near the average basic prescription for a particular population. Alternatively or additionally, the primary optic 602 may be configured to provide a predetermined optical quality over a range of expected amounts of a particular optical aberration for a particular population.

Each of the supplemental optics 604 from the set S1 of supplemental optics 604 may be configured to vary from one another in optical power by a predetermined amount. For example, the supplemental optics 604 may be configured to vary by ½ Diopter, ¼ Diopter, or less than ¼ Diopters from one another. In this manner, the primary optic 602 is implanted to provide and approximate correction of vision for the patient and a predetermined optical performance over range of accommodation add powers.

In other embodiments, the primary optic 602 is selected from plurality or set P2 of primary optics 602 and the supplemental optic 604 is selected from a set or plurality S2 of supplemental optics 604. Since there is more one primary optic 602 for providing an approximate correction of the eyes in a given population, the number of optics in the set S2 of supplemental optics 604 may be relatively small, for example as compared to the number of optics in the set S1 previously discussed. Alternatively, the optics in the sets P2 of primary optics 602 and in the set S2 of supplemental optics 604 may be configured to provide visual correction for populations having variations in basic prescription that are too large to be covered using only a single primary optic 602, as in the previous embodiment.

Figure 13:
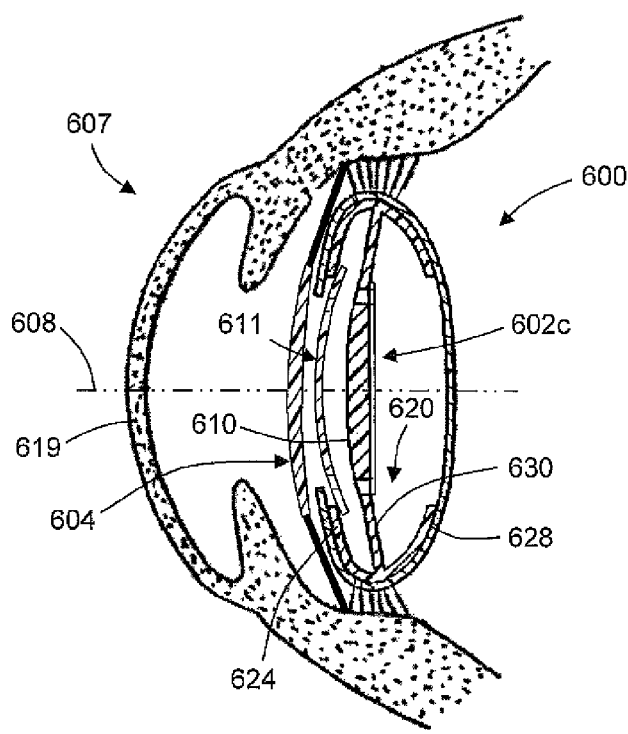
FIG. 13 is a cross-sectional view of an ophthalmic device according to an embodiment of the invention including a primary lens of FIG. 9 and a corrector optic support by the sulcus of the eye.

Referring to FIG. 13, in certain embodiments, the ophthalmic device 600 comprises a corrector optic 604c configured to correct the optical power of the primary optic 602, wherein the primary optic 602 may be configured to have a base optical power that is selected to provide a patient's basic prescription for at least one of distant vision, intermediate vision, or near vision. The corrector optic 604c may be configured to correct a monochromatic aberration and/or a chromatic aberration of, for example, the primary optic 602, the cornea 619, and/or an overall aberration of the eye 607. The corrector optic 604c may have an overall positive or negative optical power, for example, within a range of about −4 Diopters to +4 Diopters or in a range of −2 Diopters to +2 Diopters. Also, the corrector optic 604c may be a multifocal lens and/or provide cylinder correction. Alternatively, the corrector optic 604c may have no or substantially no overall optical power and be used primary to correct an aberration of primary optic 602 or the eye 607. When the corrector optic 604c has no or substantially no optical power, the primary optic 602 generally has a base optical power that provides the patient's basic prescription. In some embodiments, the basic prescription will be the basic prescription for distant vision; however, the basic prescription may alternatively the basic prescription for intermediate or near vision.

The corrector optic 604c may be disposed in the sulcus, as illustrated in FIG. 11. Alternatively, the corrector optic 604c may be disposed in the anterior chamber, similar to the location of the supplemental optic 604 in FIGS. 9 and 10. In other embodiments, the corrector optic 604c may be a corneal implant configured to be disposed within the cornea 619 or a surface profile disposed on or within the cornea 619, the profile being formed by a laser (e.g., using a LASIK, LASEK, or PRK procedure). In yet other embodiments, the corrector optic 604c is the rigid optic 611 configured to deform the primary optic 602 in a predetermined manner. In such embodiments, the optics 602, 604c are configured such that the deformable surface 610 of the primary optic 602 is deformed when the optics 602, 604c are pressed together.

The corrector optic 604c may be used to correct monochromatic and/or chromatic aberrations of the ophthalmic device 600, the eye 607 of an individual, or a population of eyes. The corrector optic 604c may be a purely refractive optical element or may additionally or alternatively comprise a diffractive element, for example, as discussed in U.S. Pat. Nos. 4,642,112, 4,881,805, and 5,144,483, which are herein incorporated by reference. Diffractive elements may be especially useful for correcting chromatic aberrations and may be configured to provide either monofocal or multifocal lens. When the corrector optic 604c is purely refractive, it may be configured to correct a chromatic aberration by combining a plurality of optical elements that are each made of a different material having different optical characteristics (e.g., different refractive indices and/or Abbe numbers). Monochromatic aberrations that may be corrected by the corrector optic 604c include, but are not limited to, astigmatic, spherical, and/or comatic. Correction of such aberrations is discussed in greater detail, for example, in U.S. Pat. Nos. 5,777,719, 6,609,793, and 6,830,332, which are herein incorporated by reference.

In some embodiments, the primary optic 602 is a corrector optic that may be used to correct or compensate for an optical aberration of the eye 607 and/or the supplemental optic 604. In other embodiments, the primary optic 602 and the supplemental optic 604 together correct or compensate for an optical aberration of at least a portion of the eye 607. For example, the primary optic 602 may be configured to correct astigmatism produced by the cornea 619, while the supplemental optic 604 is selected to correct a spherical aberration of the cornea 619. Alternatively or additionally, the primary optic 602 may be configured to correct a spherical aberration of the cornea 619 based on a preliminary estimate before the primary optic 602 is implanted into the eye 607. The supplemental optic 604 may then be select to have a spherical aberration that compensates for any remaining spherical aberrations resulting from implantation of the primary optic 602. In certain embodiments, the corrector optic 604c is selected from a plurality or set S3 of corrector optics 604c, wherein each of the corrector optics 604c from the set S3 has a predetermined value of an optical characteristic that is different from the value of that optical characteristic for the other corrector optics 604c within the set S3. At least one of the corrector optics 604c in the set S3 is configured to provide, in combination with the primary optic 602, the basic prescription of the patient for at least one of distant vision, near vision, or intermediate vision.

While this invention has been described with respect to various specific examples and embodiments, it is to be understood that the invention is not limited thereto and that it can be variously practiced within the scope of the following claims.

What is claimed is:

1. An ophthalmic device, comprising: a primary optic having a base optical power and configured for placement in a capsular bag of an eye of a patient having an optical axis; and a supplemental optic configured to be placed in an anterior chamber of the eye; and at least one fixation member coupled to the supplemental optic and configured to contact an angle of the eye; wherein the supplemental optic is maintained in a substantially stationary position in the anterior chamber and configured to correct the optical power of the primary optic, and the primary optic is configured to move axially along the optical axis in response to an ocular force of the eye.

2. The ophthalmic device of claim 1, wherein the supplemental optic has an optical power that is within the range of about −4 Diopters to about +4 Diopters.

3. The ophthalmic device of claim 1, further comprising a fixation member operably coupled to the supplemental optic.

4. The ophthalmic device of claim 1, wherein at least one surface of the primary optic is configured to deform in response to an ocular force so as to provide an add power of at least 3 Diopters.

5. The ophthalmic device of claim 1, wherein the supplemental is configured to correct at least one of a monochromatic aberration and a chromatic aberration of the primary optic and/or the eye.

6. The ophthalmic device of claim 1, wherein the monochromatic aberration is at least one of an astigmatic aberration, a spherical aberration, and a comatic aberration.

\* \* \* \* \*